US008058512B2

(12) United States Patent
Oishi et al.

(10) Patent No.: US 8,058,512 B2
(45) Date of Patent: Nov. 15, 2011

(54) GENE EXPRESSION AND PRODUCTION OF TGF-β PROTEINS INCLUDING BIOACTIVE MULLERIAN INHIBITING SUBSTANCE FROM PLANTS

(75) Inventors: Karen K. Oishi, Draper, VA (US); Leonard M. Comaratta, Blacksburg, VA (US)

(73) Assignees: David N. Radin, State University, AR (US); Carole L. Cramer, State University, AR (US)

(*) Notice: Subject to any disclaimer, the term of this patent is extended or adjusted under 35 U.S.C. 154(b) by 0 days.

(21) Appl. No.: 11/268,741

(22) Filed: Nov. 8, 2005

(65) Prior Publication Data
US 2006/0248616 A1 Nov. 2, 2006

Related U.S. Application Data

(63) Continuation of application No. 10/162,223, filed on Jun. 5, 2002, now abandoned.

(60) Provisional application No. 60/295,545, filed on Jun. 5, 2001.

(51) Int. Cl.
*C12N 15/82* (2006.01)

(52) U.S. Cl. .................. 800/288; 800/287; 435/468
(58) Field of Classification Search .............. None
See application file for complete search history.

(56) References Cited

U.S. PATENT DOCUMENTS

| | | | |
|---|---|---|---|
| 4,956,282 A | 9/1990 | Goodman et al. | |
| 5,202,422 A | 4/1993 | Hiatt et al. | |
| 5,316,931 A | 5/1994 | Donson et al. | |
| 5,550,038 A * | 8/1996 | Goodman et al. | 435/70.1 |
| 5,584,807 A | 12/1996 | McCabe | |
| 5,620,882 A | 4/1997 | John | |
| 5,639,947 A | 6/1997 | Hiatt et al. | |
| 5,689,056 A * | 11/1997 | Cramer et al. | 800/301 |
| 5,716,802 A | 2/1998 | Sijmons et al. | |
| 5,780,708 A | 7/1998 | Lundquist et al. | |
| 5,804,694 A | 9/1998 | Bruce et al. | |
| 5,889,190 A | 3/1999 | Donson et al. | |
| 5,929,304 A | 7/1999 | Radin et al. | |
| 5,959,177 A | 9/1999 | Hein et al. | |
| 5,977,438 A | 11/1999 | Turpen et al. | |
| 5,990,284 A | 11/1999 | Mahiou et al. | |
| 6,037,456 A | 3/2000 | Garger et al. | |
| 6,051,753 A | 4/2000 | Comai et al. | |
| 6,080,560 A | 6/2000 | Russell et al. | |
| 6,121,014 A | 9/2000 | Koziel et al. | |

FOREIGN PATENT DOCUMENTS

| | | |
|---|---|---|
| WO | WO 89/06695 | 7/1989 |
| WO | WO 91/19869 A1 | 12/1991 |
| WO | WO 97/38710 A1 | 10/1997 |
| WO | WO 98/10062 A1 | 3/1998 |
| WO | WO 99/66026 A2 | 12/1999 |
| WO | WO 01/29242 | 4/2001 |

OTHER PUBLICATIONS

Cate R.L. et al. Isolation of the bovine and human genes for Mullerian inhibiting substance and expression of the human gene in animal cells. Cell. Jun. 6, 1986;45(5):685-98.*
Kurian M.S. et al. Cleavage of Mullerian inhibiting substance activates antiproliferative effects in vivo. Clin Cancer Res. Mar. 1995;1(3):343-9.*
Hayashi M. et al. Immunocytochemical localization of Mullerian inhibiting substance in the rough endoplasmic reticulum and Golgi apparatus in Sertoli cells of the neonatal calf testis using a monoclonal antibody. J Histochem Cytochem. Jun. 1984;32(6):649-54.*
Iturriaga G. et al. Endoplasmic reticulum targeting and glycosylation of hybrid proteins in transgenic tobacco. Plant Cell. Mar. 1989;1(3):381-90.*
Schlunegger M.P. et al. Crystallization and preliminary X-ray analysis of recombinant human transforming growth factor beta 2. FEBS Lett. May 25, 1992;303(1):91-3.*
Nakamura M. et al. Molecular cloning and characterization of a cDNA encoding monoclonal nonspecific suppressor factor. Proc Natl Acad Sci U S A. Apr. 11, 1995;92(8):3463-7.*
Adelman et al. "In Vitro Deletional Mutagenesis for Bacterial Production of the 20,000-Dalton Form of Human Pituitary Growth Hormone", *DNA*, 1983, pp. 183-193, vol. 2, No. 3.
Alber, et al. "Nucleotide Sequence of the Triose Phosphate Isomerase gene of *Saccharmyces cerevisiae*", *Journal of Molecular and Applied Genetics*, 1982, pp. 419-434, vol. 1, No. 5.
Artsaenko, et al. "Expression of a single-chain Fv antibody against abscisic acid creates a wilty phenotype in transgenic tobacco", *The Plant Journal*, 1995, pp. 745-750, vol. 8, No. 5.
Ausubel, et al., Eds., *Current Protocols in Molecular Biology*, 1994-1998, 1-12, vol. 1, John Wiley & Sons, Inc., U.S.A.
Bevan, et al. "The structure and transcription start site of a major potato tuber protein gene", *Nucleic Acids Research*, 1986, pp. 4625-4639, vol. 14, No. 11.
Bird, R.E. et al. "Single-Chain Antigen-Binding Proteins", *Science*, 1988, pp. 423-426, vol. 242.
Bray, et al. "Expression of the β-subunit of β-conglycinin in seeds of transgenic plants", *Planta*, 1987, pp. 364-370, vol. 172, No. 3.

(Continued)

*Primary Examiner* — Cynthia Collins
(74) *Attorney, Agent, or Firm* — Saliwanchik, Lloyd & Eisenschenk

(57) ABSTRACT

This invention describes a novel method of producing bioactive recombinant proteins from plants. General methods of designing and engineering plants for expression and production of such proteins are also disclosed. Methods for the expression of Transforming Growth Factor-β (TGF-β) proteins, such as Müllerian Inhibiting Substance (MIS), in plants, and methods of producing recombinant proteins from plants are specifically disclosed. Furthermore, the present invention provides methodology for the direct expression and production of a bioactive C-terminal fragment of a TGF-β protein, such as C-terminal MIS. The new method is more cost-effective than other large-scale expression systems, by eliminating the need for costly cell culture and fermentation manufacturing facilities.

13 Claims, 16 Drawing Sheets

OTHER PUBLICATIONS

Figure 1:
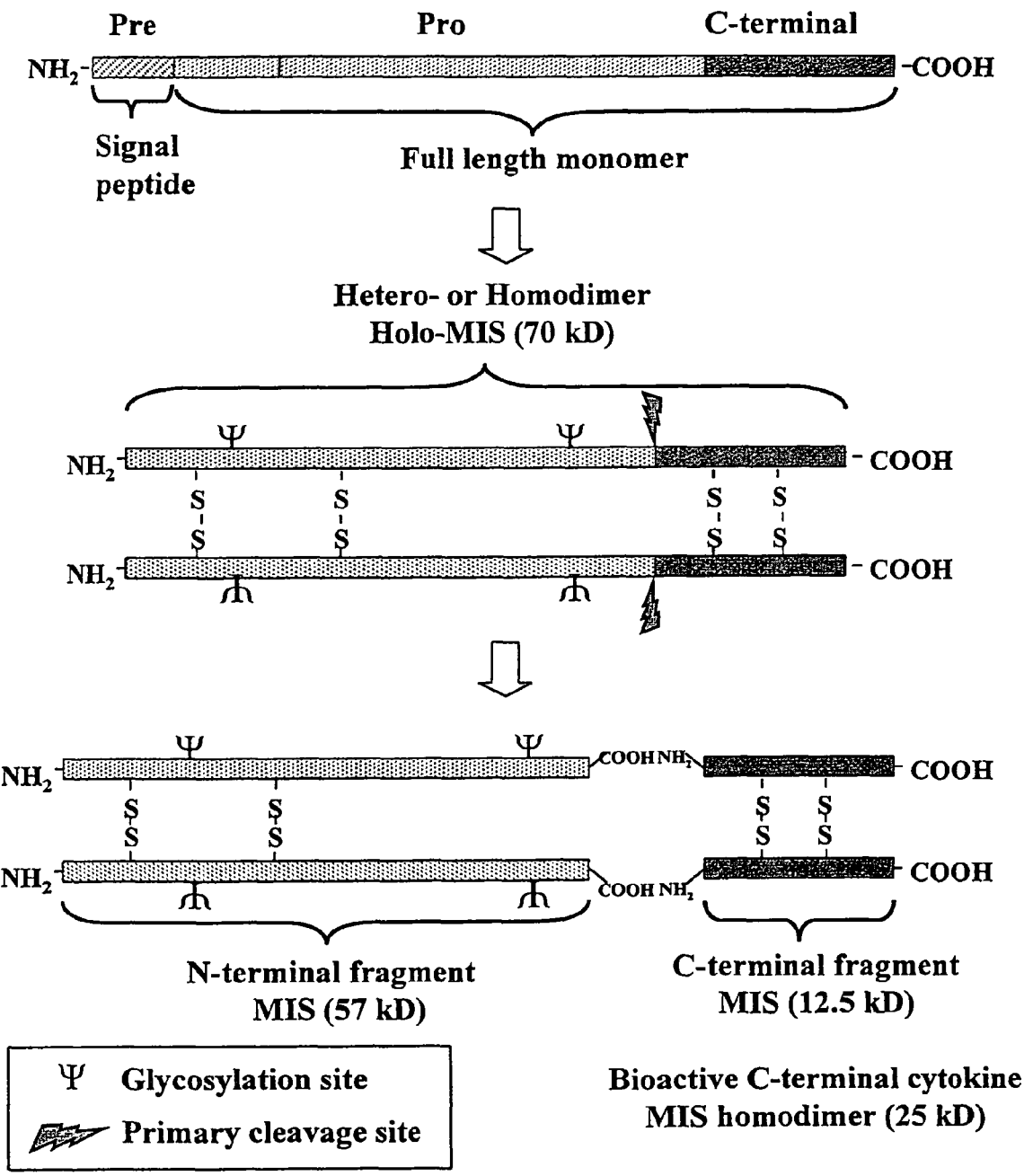

Buchanan, et al. "Reduction of Allergenicity in Plant Foods by Thioredoxin", *Plant Physiology*, 1995, p. 150, pp. 108, vol. 2.

Budzik, et al. "Enhanced Purification of Mullerian Inhibiting Substance by Lectin Affinity Chromatography", *Cell*, 1980, pp. 909-915, vol. 21, No. 3.

Casas, et al. "Transgenic soghum plants via microporjectile bombardment", *Proc. Natl. Acad. Sci. USA*, 1993, pp. 11212-11216, vol. 90.

Cate, et al. "Isolation of the Bovine and Human Genes for Mullerian Inhibiting Substance and Expression of the Human Gene in Animal Cells", *Cell*, 1986, pp. 685-698, vol. 45.

Chin, et al. "Human Mullerian Inhibiting Substance Inhibits Tumor Growth in Vitro and in Vivo", *Cancer Research*, 1991, pp. 2101-2106, vol. 51, No. 8.

Chopra, et al. Eds., *Applied Plant Biotechnology*, 1999, Science Publishers, Inc. USA.

Chrispeels & Faye, "The production of Recombinant Glycoproteins with Defined Non-Immunogenic Glycans," *Transgenic Plants: A Production System for Industrial and Pharmaceutical Proteins*, 1996, pp. 99-113, John Wiley & Sons, Ltd.

Christou, et al. "The development of a variety-independent gent-trasfer method for rice", *TIBTECH*, 1992, pp. 239-246, vol. 10, No. 6.

Conrad, et al. "Compartment-specific accumulation of recombinant immunoglobulins in plant cells: an essential tool for antibody production and immunomodulation of physiological functions and pathogen activity", *Plant Mol Bio.*, 1998, pp. 101-109, vol. 38, Nos. 1-2.

Cornejo, et al. "Activity of maize ubiquitin promoter in transgenic rice", *Plant Molecular Biology*, 1993, pp. 567-581, vol. 23, No. 3.

Crossway, et al. "Integration of foreign DNA following microinjection of tobacco mesophyll protoplasts", *Mol. Gen. Genet.*, 1986, pp. 179-185, vol. 202, No. 2.

Croy, Eds., *Plant Molecular Biology LabFax*, 1993, vii-xii, BIOS Scientific Publishers Limited, Oxford.

Depicker, et al. "*Nopaline Syntase:* Transcript Mapping and DNA Sequence", *Journal of Molecular and Applied Genetics*, 1982, pp. 561-573, vol. 1, No. 6.

Donahoe, et al. "Mullerian Inhibiting Substance Activity in Bovine Fetal, Newborn and Prepubertal Testes", *Biology of Reproduction*, 1977, pp. 238-243, vol. 16, No. 12.

Donahoe, et al. "Mullerian Inhibiting Substance Inhibits Growth of a Human Ovarian Cancer in Nude Mice", *Annals of Surgery*, 1981, pp. 427-480, vol. 194, No. 4.

Düring, et al. "Synthesis and self-assembly of a functional monoclonal antibody in transgenic *nicotiana tabacum*", *Plant Molecular Biology*, 1990, pp. 1090-1093, vol. 13.

Evans, et al. Eds., *Handbook of Plant Cell Culture*, vol. 1, *Techniques for Propagation and Breeding*, 1983, vii-viii, Macmillan Publishing Company, New York.

Fecker, et al. "Expression of single-chain antibody fragments (scFv) specific for beet necrotic yellow vein virus coat protein or 25 kDa protein in *Escherichia coli* and *Nlcotiana benthamiana*", *Plant Mol. Bio.*, 1996, pp. 979-986, vol. 32, No. 5.

Fiedler, et al. "High-Level Production and Long-Term Storage of Engineered Antibodies in Transgenic Tobacco Seeds", *Biotechnology*, 1995, pp. 1090-1093, vol. 13.

Frayley, et al. "Lipsome-mediated deliver of tobacco mosaic virus RNA into tobacco protoplasts: A sensitive assay for monitoring lipsome-protoplast interactions", *Proc. Natl. Acad. Sci. USA*, 1982, pp. 1859-1863, vol. 79.

Fromm, et al. "Expression of genes transferred into monocot and dicot plant cells by electroporation", *Proc. Natl. Acad. Sci. USA*, 1985, pp. 5824-5828, vol. 82.

Fromm, et al. "Inheritance and Expression of Chimeric Genes in the Progeny of Transgenic Maize Plants", *Bio/Technology*, 1990, pp. 833-839, vol. 8.

Fuller, et al. "Mullerian Inhibiting Substance Reduction of Colony Growth of Human Gynecologic Cancers in a Stem Cell Assay", *Gynecologic Oncology*, 1985, vol. 135-149, vol. 22, No. 2.

Galun, et al. Eds., *Transgenic Plants*, 1997, ix-xiii, Imperial College Press, London.

Gielen, et al. "The comlete nucleotide sequence of the TL-DNA of the *Agrobacterium tumefaciens* plasmid pTiAch5", *The EMBO Journal*, 1984, pp. 835-846, vol. 3, No. 4.

Gordon-Kamm, et al. "Transformation of Maize Cells and Regeneration of Fertile Transgenic Plants", *The Plant Cell*, 1990, pp. 603-618, vol. 2, No. 7.

Harlow, et al. Eds., *Antibodies A Laboratory Manual*, 1988, iii-ix, Cold Spring Harbor Laboratory, USA.

Hiatt, et al. "Production of antibodies in transgenic plants", *Nature*, 1989, pp. 76-78, vol. 342, No. 6245.

Horsch, et al. "A Simple and General Method for Transferring Genes into Plants", *Science*, 1995, pp. 1229-1231, vol. 227.

Horsch, et al. "Inheritance of Functional Foreign Genes in Plants", *Science*, 1984, pp. 496-498, vol. 223, No. 4635.

Jenkins, et al. "Getting the glycosylation right: Implications for the biotechnology industry", *Nature Biotechnology*, 1996, pp. 975-981, vol. 14, No. 8.

Kane, "Effects of rare codon clusters on high-level expression of heterologous proteins in *Escherichia coli*", *Biotechnology*, 1995, pp. 494-500, vol. 6.

Klein, et al. "High-velosciy microprojectiles for delivering nucleic acids into living cells", *Nature*, 1987, pp. 70-73, vol. 327, No. 6117.

Klein, *Immunology The Science of Self-Nonself Discrimination*, 1982, xi, John Wiley & Sons, Inc., USA.

Knudsen, et al. "Transformation of the developing barley endosperm by particle bombardment", *Planta*, 1991, pp. 330-336, vol. 185, No. 3.

Kozak, "Initiation of translation in prokaryotes and eukaryotes", *Gene*, 1999, pp. 187-208, vol. 234.

Krens, et al. "In vitro Transformation of Plant Protoplasts with Ti-plasmid DNA", *Nature*, 1982, pp. 72-74, vol. 296, No. 5852.

Kurian, et al. "Cleavage of Mullerian Inhibiting Substance Activates Antiprotliferative Effects in Vivo", *Clinical Cancer Research*, 1995, pp. 343-349, vol. 1, No. 3.

Kusnadi, et al. "Production of Recombinant Proteins in Transgenic plants: Practical Considerations", *Biotechnology and Bioengineering*, 1997, pp. 473-484, vol. 56, No. 5.

Laemmli, "Cleavage OF Structural Proteins During the Assembly of the Head of Bacteriophage T4", *Nature*, 1970, pp. 680-685, vol. 227, No. 5259.

Lazzeri, "Stable transformation of barley via PEG-induced direct DNA uptake into protoplasts", *Methods in Molecular Biology*, 1995, pp. 95-106, vol. 49.

Lee, et al. "Efficient Transformation and Regeneration of Rice Small Cell Groups", *Proc. Natl. Acad. Sci. USA*, 1991, pp. 6389-6393, vol. 88.

Lee, et al. "Establishment of a Transgenic Tobacco Cell Suspension Culture System for Producing Murine Granulocyte-Macrophage Colony Stimulating Factor", *Mol. Cells*, 1997, 783-787, vol. 7, No. 6.

Lee, et al. "Mullerian Inhibiting Substance in Humans: Normal Levels from Infancy to Adulthood", 1996, pp. 571-576, vol. 81, No. 2.

Lee, et al. "Mullerian Inhibiting Substance: A Gonadal Hormone with Multiple Functions", *Endocr. Rev.*, 1993, pp. 152-164, vol. 14, No. 2.

Ma, et al. "Assembly of Monoclonal Antibodies with IgG1 and IgA Heavy Chain Domains in Transgenic Tobacco Plants", *Eur. J. Immunol.*, 1994, pp. 131-138, vol. 24, No. 1.

MacLaughlin, et al. "Bioassay, Purification, Cloning, and Expression of Mullerian Inhibiting Substance", *Methods in Enzymology*, 1991, pp. 358-369, vol. 198.

MacLaughlin, et al. "Mullerian Duct Regression and Antiproliferative Bioactivities of Mullerian Inhibiting Substance Reside in its Carboxy-Terminal Domain", *Endocrinology*, 1992, 291-296, vol. 131, No. 1.

Mason, et al. "Expression of Hepatitis B Surface Antigen in Transgenic Plants", *Proc. Natl. Acad. Sci. USA*, 1992, pp. 11745-11749, vol. 89.

Moloney, et al. "High Efficiency Transformation of *Brassica napus* Using *Agrobacterium* Vectors", *Plant Cell Reports*, 1989, pp. 238-242, vol. 8.

Müller-Röber, et al. "One of Two Different ADP-Glucose Pyrophosphorylase Genes From Potato Responds Strongly to Elevated Levels of Sucrose", *Mol. Gen. Genet.*, 1990, pp. 136-146, vol. 224, No. 1.

Murray, et al. "Codon Usage in Plants Genes", *DNA cloning vol. iii a Practical Approach*, 1989, pp. 447-498, vol. 17, No. 2, DM Glover, Ed., IRL Press at Oxford University Press.

Owen, et al. Eds., *Transgenic Plants: A Production System for Industrial and Pharmaceutical Proteins*, 1996, v-vi, John Wiley & Sons.

Owen, et al. Eds., "Synthesis of a Functional Anti-Phytochrome Single-Chain Fv Protein in Transgenic Tobacco", *Biotechnology*, 1992, pp. 790-794, vol. 10.

Palacpac, et al. "Stable Expression of Human β1, 4-galactosyltransferase in Plant Cells Modifies N-linked Glycosylation Patterns", *Proc. Natl. Acad. Sci. USA*, 1999, pp. 4692-4697, vol. 96.

Parry, et al. "Recombinant Human Mullerian Inhibiting Substance Inhibits Human Ocular Melanoma Cell Lines in Vitro and in Vivo", *Cancer Research*, 1992, pp. 1182-1186, vol. 52, No. 5.

Pedersen, et al. "Cloning and Sequence Analysis Reveal Structural Variation Among Related Zein Genes in Maize", *Cell*, 1982, pp. 1015-1026, vol. 29, No. 3.

Perlak, et al. "Modification of the Coding Sequence Enhances Plant Expression of Insect Control Protein Genes", *Proc. Natl. Acad. Sci. USA*, 1991, pp. 3324-3328, vol. 8.

Ragin, et al. "Human Mullerian Inhibiting Substance: Enhanced Purification Imparts Biochemical Stability and Restores Antiproliferative Effects", *Protein Expression and Purification*, 1992, pp. 236-245, vol. 3.

Rayon, et al. "Characterization of *N*-Glycans form Arabidopsis. Application to a Fucose-Deficient Mutant", *Plant Physiology*, 1999, pp. 725-733, vol. 119.

Rogers, "Two Barley α-Amylase Gene Families Are Regulated Differently in Aleuron Cells", *The Journal of Biological Chemistry*, 1985, pp. 3731-3738, vol. 260, No. 6.

Russel, "Tissue-specific Expression in Transgenic Maize of Four Endosperm Promoters from Maize and Rice", *Transgenic Research*, 1997, pp. 157-168, vol. 6, No. 2.

Russel, "Feasibility of Antibody Production in Plants for Human Therapeutic Use" *Plant Biotechnology New Products and Applications*, 1999, pp. 119-138, John Hammond et al. Eds., Springer-Verlag, Germany.

Saito, et al. "Integration and Expression of a Rabbit Liver Cytochrom P-450 Gene in Transgenic *Nicotiana tabacum*" *Proc. Natl. Acad. Sci. USA*, 1991, pp. 7041-7045, vol. 88.

Schaewen, et al. "Isolation of a Mutant *Arabidopsis* Plant That Lacks N-Acetyl Glucosaminyl Transferase I and is Unable to Synthesize Golgi-Modified Complex N-Linked Glycans", *Plant Physiol.*, 1993, pp. 1109-1118, vol. 2, No. 4.

Scopes, *Protein Purification*, Charles R. Cantor, Eds., 1994, xv-xix, Springer-Verlag, USA.

Segev, et al. "Mullerian Inhibiting Substance Inhibits Breast Canter Cell Growth through an NF B-mediated Pathway", *The Journal of Biological Chemistry*, 2000, pp. 28371-28379, vol. 275, No. 37.

Sijmons, et al. "Production of Correctly Processed Human Serum Albumin in Transgenic Plants", *Bio/Technology*, 1990, pp. 217-221, vol. 8.

Stryer, *Biochemistry. 3rd Edition*, 1988, pp. 786-770, W. H. Freeman and Company/New York.

Swann, et al. "Extraction of Mullerian Inhibiting Substance form Newborn Calf Testis", *Developmental Biology*, 1979, pp. 73-84, vol. 69.

Taylor, et al. "Optimizing the Expression of Chimeric Genes in Plant Cells", *Mol. Gen. Genet.*, 1987, pp. 572-577, vol. 210.

Thèze, *The Cytokine Network and Immune Functions*, 1999, xi-xxv, Oxford University Press.

Vasil, Ed., *Cell Culture and Somatic Cell Genetics of Plants, vol. 1, Laboratory Procedures and Their Applications*, 1984, vii-xxii, Academic Press, Inc., USA.

Vasil, Ed., *Cell Culture and Somatic Cell Gentics of Plants, vol. 3, Plant Regeneration and Genetic Variability*, 1986, vii-xiv, Academic Press, Inc., USA.

Wallen, et al. "Minimal Antiproliferative Effect of Recombinant Mullerian Inhibibiting Substance on Gynecological Tumor Cell Lines and Tumor Explants", *Cancer Research*, 1989, pp. 2005-2011, vol. 49, No. 8.

Wells, et al. "Cassette Mutagenesis: An Efficient Method for Generation of Multiple Mutations at Defined Sites", *Genes*, 1985, pp. 315-323, vol. 34.

Wernsman, et al. "47. Tobacco", *Hybridization of Crop Plants*, 1980, pp. 657-699, vol. 47.

Wilkmink, et al. "Selective Agents and Marker Genes for Use in Transformation of Monocotylodonous Plants", *Plant Molecular Biology Reporter*, 1993, pp. 165-185, vol. 11, No. 2.

Zoller, et al. "Oligonucleotide-directed Mutagenesis using M13-derived Vectors: An Efficient and General Procedure for the Production of Point Mutations in any Fragment of DNA", *Nucleic Acids Research*, 1982, pp. 6487-6500, vol. 10, No. 20.

Zugmaier, et al. "Transforming Growth Factors Type Beta 1 and Beta 2 Are Equipotent Growth Inhibitors of Human Brest Cancer Cell Lines", *Journal of Cellular Physiology*, 1989, pp. 353-361, vol. 141.

Hayashi, M. et al. "Immunocytochemical Localization of Mullerian Inhibiting Substance in the Rough Endoplasmic Reticulum and Golgi Apparatus in Sertoli Cells of the Neonatal Calf Testis Using a Monoclonal Antibody", *Journal of Histochemistry and Cytochemistry*, 1984, pp. 649-654, vol. 32, No. 6.

Iturriaga, et al. "Endoplasmic Reticulum Targeting and Glycosylation of Hybrid Proteins in Transgenic Tobacco", *Plant Cell*, 1989, pp. 381-390, vol. 1. XP002306942.

Catlin, E. et al., "Mullerian inhibiting substance: new perspectives and future directions", *Microscopy Research and Technique*, 1993, pp. 121-133, vol. 25, No. 2, XP008039222.

Fairlie, W.D. et al., "Expression of a TGF-beta superfamily protein, macrophage inhibitory cytokine-1, in the yeast *Pichia pastoris*" Gene Elsevier Biomedical Press. Amsterdam, NL, 2000, pp. 67-76, vol. 254.

Cramer, C.L. et al., "Bioproduction of Human Enzymes in Transgenic Tobacco," XP-000856387, May 25, 1996.

\* cited by examiner

```
   1 atgcgggacc tgcctctcac cagcctggcc ctagtgctgt ctgccctggg ggctctgctg
  61 gggactgagg ccctcagagc agaggagcca gctgtgggca ccagtggcct catcttccga
 121 gaagacttgg actggcctcc aggcatccca caagagcctc tgtgcctggt ggcactgggc
 181 ggggacagca atggcagcag ctccccctg cgggtggtgg gggctctaag cgcctatgag
 241 caggccttcc tgggggccgt gcagagggcc cgctgggcc cccgagacct ggccaccttc
 301 ggggtctgca acaccggtga caggcaggct gccttgccct ctctacggcg gctgggggcc
 361 tggctgcggg accctggggg gcagcgcctg gtggtcctac acctggagga agtgacctgg
 421 gagccaacac cctcgctgag gttccaggag ccccgcctg gaggagctgg cccccagag
 481 ctggcgctgc tggtgctgta ccctgggcct ggccctgagg tcactgtgac gagggctggg
 541 ctgccgggtg cccagagcct ctgccctcc cgagacaccc gctacctggt gttagcggtg
 601 gaccgccctg cggggcctg gcgcggctcc gggctggcct tgaccctgca gccccgcgga
 661 gaggactccc ggctgagtac cgcccggctg caggcactgc tgttcggcga cgaccaccgc
 721 tgcttcacac ggatgacccc ggccctgctc ctgctgccgc ggtccgagcc cgcgccgctg
 781 cctgcgcacg gccagctgga caccgtgccc ttcccgccgc ccaggccatc cgcggaactc
 841 gaggagtcgc cacccagcgc agaccccttc ctggagacgc tcacgcgcct ggtgcgggcg
 901 ctgcgggtcc ccccggcccg ggcctccgcg ccgcgcctgg ccctggatcc ggacgcgctg
 961 gccggcttcc cgcagggcct agtcaacctg tcggaccccg cggcgctgga gcgcctactc
1021 gacggcgagg agccgctgct gctgctgctg aggcccactg cggccaccac cggggatcct
1081 gcgcccctgc acgacccac gtcggcgccg tgggccacgg ccctggcgcg ccgcgtggct
1141 gctgaactgc aagcggcggc tgccgagctg cgaagcctcc cgggtctgcc tccggccaca
1201 gccccgctgc tggcgcgcct gctcgcgctc tgcccaggag gccccggcgg cctcggcgat
1261 cccctgcgag cgctgctgct cctgaaggcg ctgcagggcc tgcgcgtgga gtggcgcggg
1321 cgggatccgc gcgggccggg tcgggcacag cgcagcgcgg gggccaccgc cgccgacggg
1381 ccgtgcgcgc tgcgcagct cagcgtagac ctccgcgccg agcgctccgt actcatcccc
1441 gagacctacc aggccaacaa ttgccagggc gtgtgcggct ggcctcagtc cgaccgcaac
1501 ccgcgctacg caaccacgt ggtgctgctg ctgaagatgc aggcccgtgg ggccgccctg
1561 gcgcgcccac cctgctgcgt gcccaccgcc tacgcgggca agctgctcat cagcctgtcg
1621 gaggaacgca tcagcgcgca ccacgtgccc aacatggtgg ccaccgagtg tggctgccgg
1681 tga (SEQ ID NO:1)
```

Figure 2

MeGA+AUG Promoter (pCT60)

(SEQ ID NO:2)    5' pBS-HindIII - C AATACGATAT
(SEQ ID NO:3)                        3'G TTATGCTATA

```
-336 TACCGAATAT TATACTAAAT CAAAATTTAA TTTATCATAT CGAATTATTA
     ATGGCTTATA ATATGATTTA GTTTTAAATT AAATAGTATA GcTTAATAAT

-286 AACTGATATT TCAAATTTTA ATATTTAATA TCTACTTTCA ACTATTATTA
     TTGACTATAA AGTTTAAAAT TATAAATTAT AGATGAAAGT TGATAATAAT

-236 CCTAATTATC AAATGCAAAA TGTATGAGTT ATTTCATAAT AGCCCGAGTTC
     GGATTAATAG TTTACGTTTT ACATACTCAA TAAAGTATTA TCGGGcTCAAG

-186 GTATCCAAAT ATTTTACACT TGACCAGTCA ACTTGACTAT ATAAAACTTT
     CATAGGTTTA TAAAATGTGA ACTGGTCAGT TGAACTGATA TATTTTGAAA

-136 ACTTCAAAAA ATTAAAAAAA AAAGAAAGTA TATTATTGTA AAAGATAATA
     TGAAGTTTTT TAATTTTTTT TTTCTTTCAT ATAATAACAT TTTCTATTAT

-86 CTCCATTCAA AATATAAAAT GAAAAAGTC CAGCGCGGCA ACCGGGTTCC
     GAGGTAAGTT TTATATTTTA CTTTTTTCAG GTCGCGCCGT TGGCCCAAGG

-36 TCTATAAATA CATTTCCTAC ATCTTCTCTT CTCCTCACAT CCCATCACTC
     AGATATTTAT GTAAAGGATG TAGAAGAGAA GAGGAGTGTA GGGTAGTGAG

+15 TTCTTTTAAC AATTATACTT GTCAATCATC AATCCCACAA ACAACACTTT
     AAGAAAATTG TTAATATGAA CAGTTAGTAG TTAGGGTGTT TGTTGTGAAA
                                                      XbaI
 +65 TTCTCTCCTC TTTTTCCTCA CCGGCGGCAG ACTTACCGGT GAAAtctaga
     AAGAGAGGAG AAAAAGGAGT GGCCGCCGTC TGAATGGCCA CTTTagatct
                           EcoRI
+115 gtaagcatc/at(g    aattcc)-3'   (digest with EcoRI and blunt with
     cattcgtag/ta c    ttaagg -5'   mungbean nuclease to flush AUG)
```

Figure 4

```
  1 MRDLPLTSLA LVLSALGALL GTEALRAEEP AVGTSGLIFR EDLDWPPGIP QEPLCLVALG
 61 GDSNGSSSPL RVVGALSAYE QAFLGAVQRA RWGPRDLATF GVCNTGDRQA ALPSLRRLGA
121 WLRDPGGQRL VVLHLEEVTW EPTPSLRFQE PPPGGAGPPE LALLVLYPGP GPEVTVTRAG
181 LPGAQSLCPS RDTRYLVLAV DRPAGAWRGS GLALTLQPRG EDSRLSTARL QALLFGDDHR
241 CFTRMTPALL LLPRSEPAPL PAHGQLDTVP FPPPRPSAEL EESPPSADPF LETLTRLVRA
301 LRVPPARASA PRLALDPDAL AGFPQGLVNL SDPAALERLL DGEEPLLLLL RPTAATTGDP
361 APLHDPTSAP WATALARRVA AELQAAAAEL RSLPGLPPAT APLLARLLAL CPGGPGGLGD
421 PLRALLLLKA LQGLRVEWRG RDPRGPGRAQ RSAGATAADG PCALRELSVD LRAERSVLIP
481 ETYQANNCQG VCGWPQSDRN PRYGNHVVLL LKMQARGAAL ARPPCCVPTA YAGKLLISLS
541 EERISAHHVP NMVATECGCR * (SEQ ID NO:6)
```

Figure 8

1. Patatin signal peptide : C-Terminal MIS peptide a. C-Terminal MIS peptide
```
  1 agcgcggggg ccaccgccgc cgacgggccg tgcgcgctgc gcgagctcag cgtagacctc
 61 cgcgccgagc gctccgtact catccccgag acctaccagg ccaacaattg ccagggcgtg
121 tgcggctggc ctcagtccga ccgcaacccg cgctacggca accacgtggt gctgctgctg
181 aagatgcagg cccgtggggc cgccctggcg cgcccaccct gctgcgtgcc caccgcctac
241 gcgggcaagc tgctcatcag cctgtcggag gaacgcatca gcgcgcacca cgtgcccaac
301 atggtggcca ccgagtgtgg ctgccggtga (SEQ ID NO:7)
```

```
 1 SAGATAADGP CALRELSVDL RAERSVLIPE TYQANNCQGV CGWPQSDRNP RYGNHVVLLL
61 KMQARGAALA RPPCCVPTAY AGKLLISLSE ERISAHHVPN MVATECGCR* (SEQ ID NO:8)
``` b. patatin signal peptide

```
 1 ATGGCAACTA CTAAATCTTT TTTAATTTTA TTTTTTATGA TATTAGCAAC TACTAGTTCA
61 ACATGTGCG  (SEQ ID NO:9)
```

```
1 MATTKSFLIL FFMILATTSS TCA (SEQ ID NO:10)
```

Figure 9

```
                                    5'pBS-HindIII    -C AATACGATAT
                                                   3'G TTATGCTATA -336 TACCGAATAT TATACTAAAT CAAAATTTAA TTTATCATAT CgAATTATTA
     ATGGCTTATA ATATGATTTA GTTTTAAATT AAATAGTATA GcTTAATAAT -286 AACTGATATT TCAAATTTTA ATATTTAATA TCTACTTTCA ACTATTATTA
     TTGACTATAA AGTTTAAAAT TATAAATTAT AGATGAAAGT TGATAATAAT -236 CCTAATTATC AAATGCAAAA TGTATGAGTT ATTTCATAAT AGCCCgAGTTC
     GGATTAATAG TTTACGTTTT ACATACTCAA TAAAGTATTA TCGGGcTCAAG -186 GTATCCAAAT ATTTACACT  TGACCAGTCA ACTTGACTAT ATAAAACTTT
     CATAGGTTTA TAAAATGTGA ACTGGTCAGT TGAACTGATA TATTTTGAAA -136 ACTTCAAAAA ATTAAAAAAA AAAGAAAGTA TATTATTGTA AAAGATAATA
     TGAAGTTTTT TAATTTTTTT TTTCTTTCAT ATAATAACAT TTTCTATTAT -86  CTCCATTCAA AATATAAAAT GAAAAAAGTC CAGCGCGGCA ACCGGGTTCC
     GAGGTAAGTT TTATATTTTA CTTTTTTCAG GTCGCGCCGT TGGCCCAAGG
                                                           +1
-36  TCTATAAATA CATTTCCTAC ATCTTCTCTT CTCCTCACAT CCCATCACTC
     AGATATTTAT GTAAAGGATG TAGAAGAGAA GAGGAGTGTA GGGTAGTGAG +15  TTCTTTTAAC AATTATACTT GTCAATCATC AATCCCACAA ACAACACTTT
     AAGAAAATTG TTAATATGAA CAGTTAGTAG TTAGGGTGTT TGTTGTGAAA +65  TTCTCTCCTC TTTTTCCTCA CCGGCGGCAG ACTTACCGGT GAAAtctaga
     AAGAGAGGAG AAAAAGGAGT GGCCGCCGTC TGAATGGCCA CTTTagatct
                                      patatin signal sequence
+115 gtaagcatc/a tggcaactac taaatctttt ttaatttttat tttttatgat
     cattcgtag/t accgttgatg atttagaaaa aattaaaata aaaaatacta attagcaact actagttcaa catgtcg(gt acc)-3'  (SEQ ID NO:11)
     taatcgttga tgatcaagtt gtacacgc(ca tgg)-5'  (SEQ ID NO:12)
                                      KpnI
```

Legend
+1: Transcriptional start site
Boxed sequence: ATG translation start codon
*Kpn I* site: Underlined
( ): indicates sequence removed by Mung bean nuclease prior to fusion with C- terminal MIS sequences.

Figure 10

GENE EXPRESSION AND PRODUCTION OF TGF-β PROTEINS INCLUDING BIOACTIVE MULLERIAN INHIBITING SUBSTANCE FROM PLANTS

FIELD OF INVENTION

This invention describes a novel method of producing bioactive recombinant proteins from plants. General methods of designing and engineering plants for expression and production of such proteins are also disclosed. Methods for the expression of Transforming Growth Factor-β (TGF-β) proteins, such as Müllerian Inhibiting Substance (MIS), in plants, and methods of producing recombinant proteins from plants are specifically disclosed. Furthermore, the present invention provides methodology for the direct expression and production of a bioactive C-terminal fragment of a TGF-β protein, such as C-terminal MIS. The new method is more cost-effective than other large-scale expression systems, by eliminating the need for costly cell culture and fermentation manufacturing facilities.

BACKGROUND OF THE INVENTION

Proteins of the TGF-β family function as cytokines mediating many important embryogenic and immune functions including chemotaxis, production of extracellular matrix, regulation of cell growth and differentiation, and development and regulation of the immune system. Thus, these molecules could be used in a great variety of therapies if available in sufficient quantities. Epithelial ovarian cancers, for example, are the fifth most common malignancy in women. Each year approximately 26,600 new cases of epithelial ovarian cancer are diagnosed, of which 55% die of the disease annually. Studies have shown that Müllerian Inhibiting Substance (MIS), a TGF-β family member, may potentially be an effective therapy for the highly lethal advanced ovarian carcinomas. The current production systems for MIS, including mammalian and bacterial systems, however, are not capable of providing MIS at levels required for clinical trials or commercial applications. Not only are these systems incapable of directly producing the biologically active C-terminal MIS, these systems cannot produce adequate quantities of the holo-MIS precursor and suffer from additional disadvantages as well.

Although the biotechnology industry has directed its efforts to eukaryotic hosts like mammalian cell tissue culture, yeast, fungi, insect cells, and transgenic animals, to express recombinant proteins, these hosts may suffer particular disadvantages. For example, although mammalian cells are capable of correctly folding and glycosylating bioactive proteins, the quality and extent of glycosylation can vary with different culture conditions among the same host cells. Yeast, alternatively, produces incorrectly glycosylated proteins that have excessive mannose residues, and generally exhibit limited post-translational processing. Other fungi may be available for high-volume, low-cost production, but they are not capable of expressing many target proteins. Although the baculovirus insect cell system can produce high levels of glycosylated proteins, these proteins are not secreted, however, thus making purification complex and expensive. Transgenic animal systems are hindered by lengthy lead times for developing herds with stable genetics, high operating costs, and potential contamination by prions or viruses.

Prokaryotic hosts such as *E. coli* may also suffer disadvantages in expressing heterologous proteins. For example, the post-translational modifications required for bioactivity may not be carried out in the prokaryote host. Some of these post-translational modifications include signal peptide processing, pro-peptide processing, protein folding, disulfide bond formation, glycosylation, gamma carboxylation, and beta-hydroxylation. As a result, complex proteins derived from prokaryote hosts are not always properly folded or processed to provide the desired degree of biological activity. Consequently, prokaryote hosts have generally been utilized for the expression of relatively simple foreign polypeptides that do not require post-translational processing to achieve a biologically active protein.

The biochemical, technical, and economic limitations on existing prokaryotic and eukaryotic expression systems has created substantial interest in developing new expression systems for the production of heterologous proteins. To that end, plants represent a suitable alternative to other host systems because of the advantageous economics of growing plant crops, plant suspension cells, and tissues such as callus; the ability to synthesize proteins in leaves, and storage organs like tubers, seeds, and fruits; the ability of plants to perform many of the post-translational modifications previously described, the capability of plants for protein bioproduction at very large scales; and the ability to produce the protein in an environment free of human pathogens. Plant-based expression systems may be more cost-effective than other large-scale expression systems for the production of therapeutic proteins.

The present invention contemplates producing a bioactive TGF-β protein, such as the MIS protein, in a plant host system. The MIS protein of the present invention may be any full length MIS precursor (e.g., holo-MIS), the 140 kD homodimer from which the bioactive C-terminal homodimer can be released, or the bioactive C-terminal peptide fragment which acts as a inhibitor of ovarian cancer at the desired concentration, and which under pathological conditions, modulates the functional activities of individual cells and tissues.

The MIS of the present invention belongs to the Transforming Growth Factor-beta (TGF-β) superfamily, which includes various TGF-β isoforms, GDF isoforms (Growth/Differentiation Factors), Inhibins, Activins, MIS (Müllerian Inhibiting Substance or Anti-Müllerian Hormone), BMP (bone morphogenetic proteins), dpp (decapentaplegic protein), Vg-1, and MNSF (monoclonal nonspecific suppressor factor). Proteins of this family share common features including sequence similarity, protein structure and post-translational processing, receptor interactions and biological function as cytokines. The MIS product of the present invention can act as a growth inhibitor of ovarian and other cancer cells originating in the reproductive organs of both males and females.

The MIS protein of the present invention has significant potential to serve as a novel, non-toxic and highly specific therapeutic agent for tumors of Müllerian origin. A wide variety of heterologous expression systems have been used in an attempt to increase yields of recombinant MIS protein. One system utilizes CHO cells transfected with the full length MIS coding sequence fused to the SV40 early promoter. Cate et al., 45 CELL 685-698 (1986). In this system, recombinant human MIS was secreted into the medium and recovered by immunoaffinity chromatography using a mouse monoclonal antibody to MIS. MacLaughlin et al., 131 ENDOCRINOLOGY 291-296 (1992); and Ragin et al., 3 PRO. EXPR. AND PUR. 236-245 (1992). Initial tests of the CHO-derived MIS showed that the majority of MIS was in a noncleaved (140 kD homodimer) form (Cate et al., 1986) which gave very limited antiproliferative activity in bioassays. Wallen et al., 49 CANC. RES. 2005-2011 (1989). However, additional steps involving MIS purification and proteolytic cleavage for C-terminal activation resulted in increased yields of bioactive protein. Kurian et al., 1 CLIN. CAN. RES. 343-349 (1995); and Ragin et al., 3 PRO. EXPR. AND PUR. 236-245 (1992). In vitro treatment with the protease plasmin has been used to generate complete cleavage and fully active MIS. In addition, enhanced cleavage efficiency was engineered into the MIS polypeptide by incorporating an arg-arg dibasic cleavage site in place of the native ser-arg site. Kurian et al., 1 CLIN. CAN. RES. 343-349 (1995). Stably transfected CHO lines which synthesize and secrete human holo-MIS have been developed. Kurian et al., 1995. However, scale-up to levels required for commercial production, or even for initial human clinical trials, has proven difficult and expensive using these systems. As a consequence, significant effort has been invested in analyzing alternative expression systems (E. coli, Pichia, baculovirus) for enhanced production of MIS. Although less costly, all of these systems were plagued with problems involving either production of insoluble aggregates or spurious proteolytic cleavage events and were less effective than the CHO-based expression system.

A number of additional observations support the need to search for more efficient means to produce MIS as an anti-cancer therapeutic. First, MIS activity is cleavage-dependent, and tumor cells in vitro do not have the ability to do this effectively. Thus, clinical applications may require administration of the fully activated form (C-terminal homo-dimer fragment). The apparent half-life of purified carboxyl-terminal MIS is short in vivo and thus, larger doses may be required. Attempts to express the C-terminal bioactive component directly in either bacterial or mammalian cell systems have been unsuccessful. It is not clear whether appropriate assembly of the C-terminal homo-dimer is dependent on the presence of the N-terminal pro-sequences or if its bioactivity in mammalian cells precludes effective bioproduction. The projected amounts of MIS required for initial in vitro and in vivo antiproliferative studies may be met by current protocols that involve CHO-based bioproduction of the holo-MIS and enzymatic activation in vitro. However, more effective strategies are needed to meet expected requirements for holo-MIS and carboxy-terminal MIS for later clinical trials and potential commercial markets. The method provided by the present invention will meet these needs by yielding more efficient and cost-effective means for producing bioactive therapeutic proteins that mimic the structure and biologically activity of authentic proteins.

Other objectives, features and advantages of the present invention will become apparent from the following detailed description. The detailed description and the specific examples, while indicating specific embodiments of the invention, are provided by way of illustration only. Accordingly, the present invention also includes those various changes and modifications within the spirit and scope of the invention that may become apparent to those skilled in the art from this detailed description.

SUMMARY OF THE INVENTION

The present invention provides methods for producing bioactive TGF-$\beta$ proteins in a plant host system in which the plant host system has been transformed with a chimeric nucleic acid that encodes TGF-$\beta$, the method including cultivating the transformed or transfected plant or plant cell culture under conditions that result in the expression of TGF-$\beta$ proteins in the plant host system. A further aspect of this method includes the recovery of TGF-$\beta$ proteins from the plant host system. According to the method of this invention, TGF-$\beta$ produced in the plant host system may be a full length precursor protein or a peptide fragment. Furthermore, the full length TGF-$\beta$ proteins may contain N-linked glycans which may include plant-specific sugars such as xylose and $\alpha$1,3 linked fucose. The invention also provides for production of full-length TGF-$\beta$ proteins in a plant system where the N-linked glycans may be modified in vivo or in vitro to reduce or eliminate the presence of plant-specific glycans or produced more desirable glycovariants. In a particular aspect of the present invention, the TGF-$\beta$ peptide fragment comprises the bioactive C-terminal end. In this embodiment, the bioactive C-terminus produced in the plant host system or the bioactive C-terminal fragments released from the TGF-$\beta$ proteins after cleavage may be free from plant-specific glycans, such as xylose and $\alpha$1,3-fucose. The invention also provides for production of bioactive C-terminal fragments of TGF-$\beta$ proteins in a plant system where the fragment contains N-linked glycans that may include plant-specific glycans or glycan compositions that may be modified in vivo or in vitro.

The present invention also provides methods for producing a bioactive MIS in a plant host system in which the plant host system had been transformed with a chimeric nucleic acid that encodes MIS, the method including cultivating the transformed or transfected plant or plant cell culture under conditions that facilitate the expression of MIS in the plant host system. A further aspect of this method includes the purification of MIS from the plant host system. According to the method of this invention, MIS produced in the plant host system may be a full length protein, a peptide fragment, or a genetic or chemical variant. In a particular aspect of the present invention, the MIS peptide fragment comprises the bioactive C-terminal end.

The method of the present invention employs a chimeric nucleic acid sequence that includes a first nucleic acid that regulates the transcription in the plant host system of a second nucleic acid sequence that encodes a signal sequence that is linked in reading frame to a third nucleic acid sequence that encodes MIS. In a preferred embodiment of the present invention, the third nucleic acid encodes the full length human MIS (hMIS). In yet another preferred embodiment, the third nucleic acid encodes the bioactive HMIS C-terminus. In a preferred aspect of the invention, the third nucleic acid sequence comprises the full-length protein and a cleavage site. In a still more preferred aspect of the invention, the cleavage site is specifically cleavable by enzymatic or chemical means which cleavage results in a MIS bioactive C-terminus. In another preferred aspect of the invention, the first nucleic acid is a plant-active transcription promoter. In another preferred aspect of the invention, the first nucleic acid is a plant-active transcription promoter, whether derived from plant gene sequences, plant viral sequences, non-plant gene sequences or synthetic origin, and including a constitutive promoter, a pre-harvest inducible promoter, a post-harvest inducible promoter, a developmentally regulated promoter, or a tissues-specific promoter. In a specific aspect, the plant-active promoter comprises the MEGA promoter (an MGA-inducible plant promoter). In another preferred aspect of the invention, the second nucleic acid sequence targets the protein to a sub-cellular location within the plant host system. Such targeted sub-cellular locations may include the cytosol, plastid, endoplasmic reticulum or the apoplast (extracellular space) and may enhance recombinant protein accumulation, stability, or recovery. In another preferred aspect of the method of this invention, the second nucleic acid encodes a plant-derived signal peptide. In another preferred aspect of the method of this invention, the second nucleic acid encodes the patatin signal sequence.

The method of the present invention provides for the production in a plant host system of MIS which is a member of TGF-β superfamily. In another preferred embodiment of the invention, the chimeric nucleic acid sequence is included in an expression cassette.

The invention described herein also provides a plant host system that has been transformed with a chimeric nucleic acid sequence that includes a first nucleic acid that regulates the transcription in the plant host system of a second nucleic acid sequence that encodes a signal sequence that is linked in reading frame to a third nucleic acid sequence that encodes hMIS. In a preferred embodiment of the present invention, the third nucleic acid encodes for the full-length hMIS. In yet another preferred embodiment, the third nucleic acid encodes for the hMIS C-terminus. In a preferred embodiment of the plant host system, the third nucleic acid sequence also comprises a cleavage site. In a still more preferred embodiment of the invention, the cleavage site is cleavable by enzymatic or chemical means, which cleavage results in the production of a MIS bioactive C-terminus. In another preferred embodiment of the invention, the first nucleic acid is a plant-active transcription promoter. In another preferred aspect of the plant host system, the second nucleic acid sequence targets the protein to a sub-cellular location within the plant host system. Such sub-cellular locations are preferably the cytosol, plastid, endoplasmic reticulum, or apoplast. In another preferred embodiment of this invention, the second nucleic acid encodes a plant-derived signal peptide. In another preferred aspect of the method of this invention, the second nucleic acid encodes a patatin signal sequence.

Additionally, the plant host system of the present invention provides for the production in a plant host system of MIS which belongs to the TGF-beta superfamily. Moreover, the full-length hMIS protein or bioactive MIS protein C-terminal fragment may be purified from the plant host system. Furthermore, the full length hMIS may contain N-linked glycans which may include plant-specific sugars such as xylose and α1,3 linked fucose. The invention also provides for production of full-length MIS in a plant system where the N-linked glycans may be modified in vivo or in vitro to reduce or eliminate the presence of plant specific glycans. Furthermore, in this embodiment the hMIS C-terminus produced in the plant host system or the hMIS C-terminus released from the holo-MIS after cleavage is free from plant-specific glycosylations, such as xylose and α1,3-fucose.

The invention embodied herein also contemplates a plant, plant cell culture, or plant seed transformed with this chimeric nucleic acid sequence. The invention herein also contemplates a full length holo-MIS protein or bioactive MIS protein C-terminal fragment produced in a plant that has been transformed by the chimeric nucleic acid sequence described herein.

BRIEF DESCRIPTION OF THE DRAWINGS

FIG. 1 illustrates the general features of proteins of the TGF-β superfamily including pre-, pro-, and bioactive domains, dimerization, and sulfide bonding, and cleavage site for release of the bioactive C-terminal fragment.

FIG. 2 depicts the full length nucleotide sequence of human MIS cDNA (SEQ ID NO:1). The nucleotide sequence is 1683 nucleotides in length.

FIG. 3 illustrates the general cloning strategy to generate the expression cassette containing the full length hMIS gene. The full length hMIS gene is fused to the MEGA wound-inducible promoter (an MGA-inducible plant promoter).

FIG. 4 depicts the MEGA promoter (an MGA-inducible plant promoter):MIS coding junction. The coding junction is designated in bold type face.

FIG. 5 illustrates sites within the DNA sequence of human pro-MIS having codons that are infrequently used (low preference codons) in tobacco protein-coding regions FIG. 6 illustrates the Western blot analysis of the holo-hMIS protein produced from transgenic tobacco plants.

FIG. 6A shows 20 μg of total protein from transgenic plant line CT102-0018 induced for 24, 48, and 72 hours. CT102-18 was analyzed on a 10-20% SDS-PAGE and probed with rabbit anti-C-terminal MIS. The boxed region for each time point was extracted using a razor blade and the proteins were then leached out of the gel by exposing to sample buffer and 120 mM DTT.

FIG. 6B depicts a Western blot were the samples were probed with rabbit anti-holo-MIS. Two dominant bands of 69 and 66 kD cross reacted with the anti-holo-MIS. These bands represent the monomer MIS protein.

FIG. 7 illustrates the general cloning strategy to generate the expression cassette containing the C-terminal hMIS gene. The coding region for C-terminal hMIS is ligated to DNA comprising the MEGA wound-inducible promoter and sequences encoding the patatin signal sequence such that there is an in-frame fusion of C-terminal MIS to the plant signal peptide FIG. 8 shows the amino acid sequence of the full length hMIS (SEQ ID NO:6).

FIG. 9 shows the nucleotide sequence of the C-terminal MIS clone (SEQ ID NO:7).

FIG. 10 depicts the MEGA promoter (an MGA-inducible plant promoter):patatin sequence:MIS coding junction. The coding junction is designated in bold type face.

FIG. 11 shows a Northern blot of total RNA isolated from wound-induced transgenic plants (#1 and #2) containing the C-terminal MIS construct. The Northern blot shows that the cross-hybridizing C-terminal MIS RNA produced in tobacco migrated to the expected size of 650 nucleotide bases.

FIG. 12 illustrates a Western blot analysis of proteins secreted for 0 to 96 hours from CT116-0036 plants after induction. Western analysis of 15% SDS-PAGE and probed with rabbit anti-C-terminal MIS. A 25 kD cross-reacting band is present in 48 to 96 hours post-induction. The bands are the expected size for the homodimer C-terminal fragment. The C-terminal MIS monomer protein should be approximately 12.5 kD. A 13 kD protein is shown in the 72 and 96 hour samples.

FIG. 13 depicts the silver-stained SDS-PAGE gel of proteins fraction from DEAE-cellulose chromatography demonstrating the presence and enrichment of the 25 kD C-terminal MIS. Secreted fractions derived from wound-induced leaves of C-terminal MIS transgenic plant line CT116-0036 were further fractionated on DEAE cellulose and proteins were subjected to SDS-PAGE under non-reducing conditions prior to detection of total protein with silver stain. The column was equilibrated with 20 mM HEPES, pH 8.5, 50 mM NaCl. Gel and samples were run with SDS present but without reductant on a 15% SDS-PAGE. Silver staining of total proteins on the gel revealed bands in the 150 mM and 250 mM NaCl washes that migrated at approximately 25 kDa. The boxed 25 kD bands cross-reacted with anti-MIS antibodies of parallel immunoblots (not shown).

FIG. 14 depicts the Müllerian Duct Regression Assay showing bioactivity of plant-derived C-terminal MIS. Proteins secreted from wound-induced transgenic tobacco leaves were recovered, filtered, concentrated and subjected to wheat germ lectin affinity chromatography prior to use in the MIS bioassay. (Donahoe et al., 16 BIOL. REPRO. 238-243 (1977); MacLaughlin et al. 198 METH. ENZYMOL. 358-369 (1991). Urogenital ridges were dissected from 14.5 day old female fetal rats and placed on agar-coated stainless steel grids and incubated with sample to be tested. After 72 hr, specimens were fixed in formalin, embedded in paraffin, sectioned into 8 mm serial sections from the cephalic end of the duct, and stained.

Figure 14A:

FIG. 14A: tissues incubated with 18 µg of the lectin column Tris wash fraction of plant extract from full length MIS transgenic plant line CT102-0018. The fraction was not activated with plasmin so no MIS activity was expected. Similar results were seen with analogous fractions from non-transgenic control tobacco plants and transgenic plants which contained an "empty" vector.

Figure 14B:
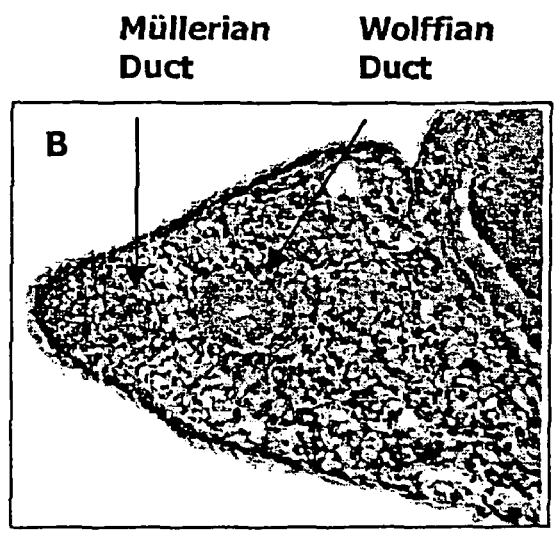

FIG. 14B: tissue incubated with 18 µg protein of the analogous Tris column wash of plant extract from C-terminal MIS transgenic plant line CT116-0036. This fraction clearly demonstrated MIS bioactivity as detected by significant regression (shrinking) of the Müllerian duct with no impact on surrounding tissues or on the adjacent Wolffian duct.

BRIEF DESCRIPTION OF THE SEQUENCES

SEQ ID NO:1 depicts the full length nucleotide sequence of human MIS cDNA. The nucleotide sequence is 1683 nucleotides in length.

SEQ ID NO:2 depicts the McGA™ promoter:MIS coding junction.

SEQ ID NO:3 depicts the complementary sequence of the McGA™ promoter:MIS coding junction.

SEQ ID NO:4 shows the nucleotide sequence for the MS3 5' primer.

SEQ ID NO:5 shows the nucleotide sequence for the MS4 3' primer.

SEQ ID NO:6 shows the amino acid sequence of the full length hMIS.

SEQ ID NO:7 shows the nucleotide sequence of the C-terminal MIS clone.

SEQ ID NO:8 shows the amino acid sequence of the C-terminal MIS peptide.

SEQ ID NO:9 shows the nucleotide sequence of the patatin signal peptide.

SEQ ID NO:10 shows the amino acid sequence of the patatin signal peptide.

SEQ ID NO:11 depicts the McGA™ promoter:patatin sequence:MIS coding junction.

SEQ ID NO:12 depicts the complementary sequence of the McGA™ promoter:patatin sequence:MIS coding junction.

DETAILED DESCRIPTION OF THE INVENTION

It is understood that the present invention is not limited to the particular methodology, protocols, cell lines, vectors, and reagents, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include plural reference unless the context clearly dictates otherwise. Thus, for example, a reference to "a protein" is a reference to one or more proteins and includes equivalents thereof known to those skilled in the art and so forth. Indeed, one skilled in the art can use the methods described herein to produce any protein of the TGF-β superfamily (known presently or subsequently) in plant host systems.

Transgenic plants have been studied for several years for potential use in low-cost production of high quality, biologically active mammalian proteins. For example human serum albumin (HSA) has been successfully secreted into the medium from plant cells derived from both potato and tobacco plants. Sijmons et al., 8 BIO/TECH. 217-21 (1990). Additionally, various other proteins have been successfully produced in plants. See, e.g., Kusnadi et al., 56(5) BIOTECH. & BIOENG'G 473-84 (1997); U.S. Pat. No. 5,550,038. Human serum albumin, transgenic plant rabbit liver cytochrome P450, hamster 3-hydroxy-3-methylglutaryl CoA reductase, and the hepatitis B surface antigen have been reported in the art. See, e.g., Sijmons, 1990; Saito et al., 88 P.N.A.S. 7041-45 (1991); Mason et al., 89 P.N.A.S. 11745-49 (1992). Additionally, low level expression of murine GM-CSF has been reported in tobacco cell suspension culture, although the protein was not characterized. L1 et al., 7(6) MOL. CELLS 783-787 (1997).

Additionally, expression of monoclonal antibodies in plant host systems has been widely studied primarily due to their potential value as therapeutic and clinical reagents. See Düring & Hippe, 370 BIOL. CHEM. HOPPE SEYLER 888 (1989); Düring et al., 15 PLANT MOL. BIOL. 281-93 (1990). These plant host systems include *Nicotania tabacum* (tobacco) plants, capable of expressing IgG antibodies. Hiatt et al., 342 NATURE 76-78 (1989); Ma et al., 24 EUR. J. IMMUNOL. 131-38 (1994); U.S. Pat. Nos. 5,202,422 and 5,639,947. More recently, a more complex secretory IgA antibody was synthesized in transgenic tobacco plants. U.S. Pat. No. 5,959,177. The synthesis of IgA in rice has been reported recently as well. WO 99/66,026. Antibodies expressed in *Zea mays* (corn) plants include monoclonal antibody BR96 and monoclonal antibody NeoRx451 (WO 98/10,062).

Single-chain antibody fragments are well-known in the art. Bird et al., 242 SCI. 423-26 (1988). Functional single chain fragments have been successfully expressed in the leaves of tobacco and *Arabidopsis* plants. Owen et al. 10 BIO/TECH. 790-94 (1992); Artsaenko et al., 8 PLANT J. 745-50 (1995); Fecker et al., 32 PLANT MOL. BIOL. 979-86 (1996). Long term storage of single chain antibody fragments has also been indicated in tobacco seeds. Fielder et al. 13 BIO/TECH. 1090-93 (1995). L6 sFv single chain anti-carcinoma antibody, anti-TAC sFv (that recognizes L2 receptor) and G28.5 sFv single-chain antibody (that recognizes CD40 cell surface protein) have been produced in high levels in tobacco culture. U.S. Pat. No. 6,080,560. Additionally, the single-chain antibody L6 has been successfully produced in corn and soy. Cooley et al., 108(2) PLANT PHYSIOL. 50 (1995).

As discussed above, most studies of transgenic plant-based expression of heterologous proteins have been performed in tobacco. It is desirable to express recombinant proteins in tobacco because (1) it is the easiest crop to genetically engineer, (2) its codon usage/preference is generally very similar to humans, (3) a single plant produced up to a million seeds (Wernsman and Matzinger, TOBACCO in HYBRIDIZATION OF CROP PLANTS pp. 657-668 (Fehr and Hadley, eds. 1980)) greatly facilitating rapid scale-up, and (4) it is an excellent biomass producer.

The present invention contemplates the use of the MEGA-PHARM (Mechanical Gene Activation—Post-Harvest Manufacturing) system for the production of the holo and C-terminal MIS proteins, which utilizes an inducible post-harvest promoter. The inducible MEGA promoter (an MGA-inducible plant promoter) (U.S. Pat. No. 5,689,056, herein incorporated by reference) was derived from a defense-associated gene, tomato HMG2. The preferred signal utilized for the rapid induction of the MEGA promoter (an MGA-inducible plant promoter) is a localized wound (within 1.5 mm). Once stably transformed seeds have been generated, the biomass can be grown under field or greenhouse conditions. The MEGA promoter (an MGA-inducible plant promoter) has very limited expression during normal growth and development. However, the MEGA promoter (an MGA-inducible plant promoter) can be activated to high levels following local wound induction. For recombinant protein production, transgenic tobacco biomass (all above ground parts) that has been harvested is mechanically wounded by shredding into 1.5 mm strips and incubated for up to 6 days at room temperature. During this incubation period, the promoter is activated, resulting in high-level production of the recombinant protein which is secreted into the apoplastic (extracellular) space. In a specific embodiment, the harvested biomass may be processed immediately or stored at 4. degree. C. for several weeks with no loss in the potential to produce transgenic protein.

After an optimum induction period resulting in maximum accumulation and secretion of the recombinant protein, the protein is recovered by rinsing the biomass and collecting the buffer. This buffer (termed the "secreted fraction") is immediately concentrated by ultrafiltration and microfiltered (NC-SRT, Inc) to remove bacteria and cell debris. By employing this system, the majority of the recombinant protein may be recovered in this secreted fraction eliminating the need to homogenize the biomass.

The apoplast is an excellent compartment for short-term in situ accumulation and storage of recombinant proteins. It has been shown that targeting of recombinant immunoglobulins (MAb) to the apoplast significantly increased protein yields in comparison to plants where MAb was targeted to the cytosol. Conrad and Fiedler, 38 PLANT MOL. BIOL. 101-109 (1998). Therefore, synthesis and assembly of hMIS in the tobacco endomembrane system and secretion using the MEGA-PHARM system may enhance the accumulation and recovery of hMIS. The MEGA-PHARM system has been successfully used to express recombinant proteins in tobacco. For example, two human lysosomal enzymes, glucocerebrosidase and .alpha.-L-iduronidase, with potential as replacement enzyme therapeutics for rare human genetic diseases were produced and found to be properly assembled as well as biologically active. See, e.g., U.S. Pat. No. 5,929,304. Human glucocerebrosidase was produced at 10% of total soluble protein in wound-induced tobacco leaves. That is, a single tobacco plant was able to produce this protein in an amount that could only be extracted from 400-1000 placentae, the original source for this therapeutic.

In the broadest aspect, the present invention provides methods for producing and recovering recombinant proteins belonging to the TGF-.beta. gene superfamily from a plant host system. This family includes Inhibins, Activins, MIS (Mullerian inhibiting substance), BMP (Bone Morphogenetic Proteins), and MNSF (monoclonal nonspecific suppressor factor). TGF-.beta. is a potent known growth inhibitor for normal and transformed epithelial cells, endothelial cells, fibroblasts, neuronal cells, lymphoid cells and other hematopoietic cell types, hepatocytes, and keratinocytes. (See website <copewithcytokines.de/>).

The proteins of the TGF-β superfamily are disulfide-linked homo- or heterodimers that are expressed as large precursor polypeptide chains containing a hydrophobic signal sequence, a long and relatively poorly conserved N-terminal pro region of several hundred amino acids, a cleavage site, and a mature domain comprising an N-terminal region which varies among the family members and a more highly conserved C-terminal region (FIG. 1). This C-terminal region, present in the processed mature proteins of all known family members, contains approximately 100 amino acids with a characteristic cysteine motif having a conserved six or seven cysteine skeleton. Although the position of the cleavage site between the mature and pro regions varies among the family members, the cysteine pattern of the C-terminus of all of the proteins is in the identical format, ending in the sequence Cys-X-Cys-X, Ser. Lechleider and Roberts, TRANSFORMING GROWTH FACTOR-β in THE CYTOKINE NETWORK AND IMMUNE FUNCTIONS (Theze, ed., Oxford Univ. Press, N.Y. 1999).

TGF-.beta. represents the prototypical cytokines of the TGF-.beta. superfamily. The various TGF-.beta. isoforms share many biological activities and their actions on cells are qualitatively similar in most cases although there are a few examples of distinct activities. The biologically active forms of all isoforms are disulfide-linked homodimers. The isoforms of TGF-beta arise by proteolytic cleavage of longer precursors (TGF-.beta.-1:390 amino acids, TGF-beta-2:412 amino acids, TGF-beta-3:412 amino acids, TGF-.beta.-4:304 amino acids, TGF-beta-5:382 amino acids). The isoforms are derived from the carboxy-terminal ends of these precursors. In yet a further embodiment, the present invention contemplates producing and recoverying a full length protein that is a member of the TGF-.beta. superfamily or the biologically active C-terminal end of the protein belonging to the TGF-.beta. superfamily from a plant host system. (See website <copewithcytokines.de/>.

In a preferred aspect of the present invention, recombinant protein includes a full-length protein or bioactive protein C-terminal fragment. In a particular embodiment of the present invention, the recombinant protein is capable under both normal and pathological conditions of modulating the activities of individual cells and tissues. In yet another preferred embodiment of the present invention, the recombinant proteins of the present invention may be any mammalian soluble protein or peptide which is capable of inhibiting cancer in vivo at the desired concentration. In a specific embodiment of the present invention, recombinant protein is used as an effective therapeutic agent against epithelial ovarian cancer. In a further embodiment of the present invention, recombinant protein may be used as an effective agent against uterine cancers, fallopian tube cancers and other cancers of tissues derived form the Mullerian duct or having cells that express the MIS receptor protein.

A preferred aspect of the present invention relates to the production of bioactive, MIS from a plant host system. The MIS protein is a member of the TGF-β family of human growth and differentiation factors. MIS is produced by the embryonic testis and causes regression of the Müllerian duct, the anlagen of the Fallopian tubes, uterus, upper vagina, and the outer lining of the ovary. Like other TGF-β growth regulators, the synthesis of MIS is quite complex. The protein is produced as a 140,000 kD sulfhydryl-linked homodimer containing two N-linked glycans. Further proteolytic processing is required to release the bioactive 25 kD C-terminal fragment (a homodimer of 12.5 kD fragment, C-term) although this fragment may retain association with the N-terminus after cleavage. Purified MIS shows cell-specific antiproliferative activity both in vitro and in vivo, causing regression of the rat Müllerian duct in organ culture and potent inhibition of human endometrial, cervical, and ovarian tumor cell lines of Müllerian/coelomic epithelium origin and tumor growth in vivo. Chin et al., 51 CANC. RES. 2101-2106 (1991); Donahoe et al., 194 ANN. SURG. 472-480 (1981); Fuller et al., 22 GYNECOL. ONCOL. 135-148 (1985); Kurian et al., 1 CANC. RES. 343-349 (1995); Laemmli, 227 NATURE 680-685 (1970). Development of biological modifiers such as MIS for cancer chemotherapy is particularly attractive because of the anticipated specificity and lack of toxicity. Thus, MIS has significant potential to serve as a novel, non-toxic therapeutic agent for tumors of Müllerian origin.

The presence of MIS in the serum of both males and females post-regression and maturation of the Müllerian duct (Lee et al, 81 J. CLIN. ENDOCRINOL. AND METAB. 571-576 (1996)) suggested that MIS may be a multifunctional growth regulator. MIS plays a role in inhibition of oocyte meiosis, inhibition of epidermal growth factor receptor autophosphorylation, and fetal lung surfactant development and thus has potential for additional medical applications, e.g., MIS also inhibits growth of human ocular melanoma cell lines. Parry et al., 52 CANC. RES. 1182-1186 (1992). The finding that MIS inhibits the growth of breast cancer cells through the NF-κB-mediated pathway has added to the exceptional promise of human MIS in chemotherapeutic treatment of ovarian, fallopian, uterine cancers, other Müllerian-derived tumors, and breast cancer and has driven the development of recombinant bioproduction systems. Segev et al., 275 JBC 28371-28329 (2000). Sufficient recombinant human MIS from Chinese hamster ovary (CHO) cell cultures has been purified to initiate toxicity studies and phase I human clinical trials. However, difficulties and costs associated with CHO-based bioproduction are limiting progress in testing this potential chemotherapeutic and are inhibiting industrial commitment toward commercialization of recombinant MIS.

In a preferred aspect of the present invention, recombinant protein includes a full-length hMIS protein or bioactive hMIS protein C-terminal fragment. In a particular embodiment of the present invention, the hMIS protein is capable under both normal and pathological conditions of modulating the activities of individual cells and tissues. In yet another preferred embodiment of the present invention, the recombinant hMIS of the present invention is capable of inhibiting cancer in vivo at the desired concentration. In a specific embodiment of the present invention, recombinant hMIS is used as an effective therapeutic agent against epithelial ovarian cancer. In a further embodiment of the present invention, recombinant hMIS may be used as an effective agent against uterine cancers, fallopian tube cancers and other cancers of tissues derived form the Mullerian duct or having cells that express the MIS receptor protein.

The bioactive MIS C-terminus does not contain sites for N-linked glycosylation. However, holo-MIS and other TGF-β full length and C-terminal proteins are glycosylated. Although plants glycosylate human proteins at the correct position, the composition of fully processed complex plant glycans differs from mammalian N-linked glycans. Plant glycans do not have the terminal sialic acid residue common in animal glycans and often contain a xylose or fucose residue with a linkage that is generally not found in mammals (Jenkins et al., 14 NATURE BIOTECH 975-981 (1996); Chrispeels and Faye in TRANSGENIC PLANTS pp. 99-114 (Owen, M. and Pen, J. eds. Wiley & Sons, N.Y. 1996; Russell 240 CURR. TOP. MICROBIO. IMMUNOL. (1999). The presence of xylose/fucose residues has been associated with antigenic responses when injected into rabbits (Chrispeels and Faye, supra). However, this same response is not seen in mice injected with plant glycoproteins or mammalian glycoproteins synthesized in plants (Oishi and Chen, unpublished results; J. Ma, Guy's Hospital, London, UK, personal communication). The composition and heterogeneity of glycosylated mouse IgGs produced in transgenic tobacco plants has been described. Cabanes-Macheteau et al., 119 PLANT PHYS 725-734 (1999). The majority (60%) of the glycans were of the complex form, contained xylose and α1,3-fucose, and lacked galactoses, which are thought to play a role in IgG-complement interactions.

The present invention contemplates the use of three strategies to address the issue of "humanization" of glycans of TGF-β products made in plants. A particular embodiment of the present invention focuses on modifications of the glycan processing machinery of tobacco. This is feasible in plants because 1) complex glycans are not critical for growth and development (van Schaewen et al., 102 PLANT PHYS 1109-1118 (1993)), and 2) glycan processing is highly sequential and compartmentalized, facilitating metabolic engineering. Tobacco α-mannosidase I and N-acetylglucosaminyltransferase I sequences have been isolated and are being utilized in anti-sense strategies to inhibit their activity in transgenic plants. The predicted impact will be a mannose-terminated glycan that lacks the unusual xylose and fucose residues found on plant complex glycans.

Furthermore, the present invention contemplates strategies that involve addition of human glycan processing enzymes. A recent report described experiments demonstrating that expression of human β-1,4-galactosyl-transferase in tobacco cells yielded N-linked glycans having a much more "human" composition. Palacpac et al., 96 P.N.A.S. 4692-4697 (1999). Less than 7% contained xylose and almost 50% had terminal galactoses. One embodiment of the present invention is to develop tobacco lines that will provide specific and homogeneous "designer" glycans in vivo that will meet the pharmacological demands of key product classes (including hMIS).

The present invention also contemplates strategies that involve in vitro modification of glycans of recombinant proteins. In such an embodiment, the glycan complement of recombinant proteins purified from the plant host system may be treated by chemical or enzymatic methods (e.g. with glycosidases such as xylosidases or 1,3 fucosidases, or glycosyltranferases such as galactosyltransferase or sialyltransferase) to produce the desired glycans.

In accordance with the present invention, methods and materials are provided for modifying expression vector design to increase yield and improve quality of hMIS expressed in a plant host system. The present invention contemplates optimizing expression vector design by modifying promoters, 5'UTRs, signal sequences, structural genes, and 3'UTRs. The design parameters of the present invention may include, but are not limited to codon usage, primary transcript structure, translational enhancing sequences, appropriate use of intron splice sites, RNA stabilizing, RNA destabilizing/processing sequences.

In a further aspect, N- or C-terminal fusions may also be established to facilitate optimal yield, quality, and protein processing. The present invention contemplates the recombinant hMIS fused to signal peptides, such as patatin, to (1) target the expressed hMIS to specific sub-cellular locations within the plant host system, (2) enhance product accumulation and quality, and (3) provide a means for simple recovery of the recombinant hMIS from the plant host system.

In accordance with further embodiments of the present invention, methods and materials are provided to optimize gene expression and protein production and accumulation so as to produce hMIS that can be easily purified from a plant host system. The expression vector design may be modified to maximize RNA transcription and translation (protein expression), protein targeting (e.g., nucleus, plastid, cytosol, endoplasmic reticulum, apoplast), protein modification and fusion, protein expression in different plant tissues, and protein expression in different plant species.

In accordance with one aspect of the present invention, methods and materials are provided for a novel means of production of recombinant hMIS in a plant host system that is easily separated from the plant host system. Purification of the recombinant hMIS is greatly simplified by this approach. The recombinant nucleic acid encoding the hMIS may be part of or all of a naturally occurring DNA sequence from any source, it may be a synthetic DNA sequence or it may be a combination of naturally occurring and synthetic sequences. The present invention includes the steps, singly or in sequence, of preparing an expression vector that includes a first nucleic acid sequence that regulates the transcription of a second nucleic acid sequence encoding a significant portion of a peptide that targets a protein to a sub-cellular location, and, fused to this second nucleic acid, a third nucleic acid encoding hMIS; generating a transformed plant host system in which hMIS is expressed; and extracting and/or recovering the hMIS from the transgenic plant host system.

In one aspect of the present invention, the first nucleic acid sequence may comprise a plant active promoter, such as the MEGA wound-inducible promoter, the second nucleic acid sequence may comprise additional 5' regulatory sequences or encode protein targeting sequences, and the third nucleic acid sequence may comprise full length hMIS or the C-terminal region of hMIS. The second nucleic acid sequences may encode signal sequences which target the protein to a specific sub-cellular location within the plant host system. In one preferred embodiment of the present invention, the nucleic acid sequence encoding the protein of interest may be fused to a sequence encoding a signal peptide that targets the protein of interest to the endoplasmic reticulum. In another embodiment of the present invention, a nucleic acid sequence encoding hMIS may be expressed without pre-sequences or targeting signals allowing significant accumulation of the mature protein in the cytosol.

In accordance with another aspect of the present invention, a plant host system is contemplated that has already been transformed with an expression vector comprising a first nucleic acid sequence that regulates the transcription of a second nucleic acid sequence encoding a significant portion of a peptide that targets a protein to a sub-cellular location and fused to this second nucleic acid, a third nucleic acid encoding full length hMIS or the C-terminal region of hMIS. In yet a further aspect, the second nucleic acid sequence encoding a TGF-β protein, i.e., MIS, may be expressed without a Pre-sequence, allowing the full length TGF-β protein to accumulate in the intracellular space. Additionally, the TGF-β protein, i.e., MIS, that has accumulated in the intracellular space may be recovered from the intracellular space by washing shredded leaf material. Likewise, the C-terminus of a TGF-β protein, such as C-terminal MIS, may be expressed without a Pre-sequence, allowed to accumulate in the intracellular space. Following accumulation, the C-terminal fragment of the TGF-β protein may be recovered from the intracellular space by washing shredded leaf material.

Another aspect of this embodiment of the present invention comprises cultivating the plant host system under the appropriate conditions to facilitate the expression of full length hMIS or the C-terminal region of hMIS, and recovering the recombinant full length hMIS or the recombinant C-terminal region of hMIS from the plant host system.

In accordance with yet another aspect of the present invention, methods and materials are provided to improve the quality and yield of the recombinant hMIS produced in a plant host system. The present invention contemplates generating a recombinant C-terminal region of the holo hMIS that is free of plant specific glycosylations, such as fucose and xylose.

The transformed or transfected plant host system of the present invention may be any monocotyledonous or dicotyledonous plant or plant cell. The monocotyledonous plants include, but are not limited to, corn, cereals, grains, grasses, and rice. The dicotyledonous plants may include, but are not limited to, tobacco, tomatoes, potatoes, and legumes including soybean and alfalfa.

Definitions

Amino acid sequences: as used herein, includes an oligopeptide, peptide, polypeptide, or protein sequence, and fragment thereof, and to naturally occurring or synthetic molecules.

Asexual propagation: producing progeny by regenerating an entire plant from leaf cuttings, stem cuttings, root cuttings, single plant cells (protoplasts) and callus.

Authentic: as used herein, means of the naturally occurring form(s), being appropriately folded, having the appropriate disulfide bonds or other post-translational modifications.

Bioactive: as used herein, means that protein, peptide or fragment thereof displays a measurable biological response in vitro or in vivo.

Chemical derivative: as used herein, a molecule is said to be a "chemical derivative" of another molecule when the chemical structure of the original molecule has been modified. Such derivations can improve the molecule's solubility, absorption, biological half-life, and the like. The derivative can alternatively decrease the toxicity of the original molecule, eliminate or attenuate any undesirable side effect of the molecule, and the like.

C-terminal MIS: refers to the bioactive C-terminal fragment (a homodimer of 12.5 kD fragment, C-term) of about 25 kD. In a particular aspect of the present invention, the C-terminal MIS shows cell-specific antiproliferative activity both in vitro and in vivo, causing regression of the rat Müllerian duct in organ culture and potent inhibition of human endometrial, cervical, and ovarian tumor cell lines of Müllerian/coelomic epithelium origin and tumor growth in vivo.

Dicotyledon (dicot): a flowering plant whose embryos have two seed halves or cotyledons. Examples of dicots include: tobacco; tomatoes; potatoes, the legumes including alfalfa and soybeans; oaks; maples; roses; mints; squashes; daisies; walnuts; cacti; violets; and buttercups.

Expression: refers to the biosynthesis of a gene product. For example, in the case of a structural gene, expression involves the transcription of the structural gene into mRNA and the translation of mRNA into one or more polypeptides.

Expression control sequences: refers to those sequences which are standard and known to those in the art, that may be included in the expression vectors to increase and/or maximize transcription or translation of the protein of interest in a plant host system. These include, but are not limited to, transcriptional enhancers, translational enhancers, peptide export signal sequences, optimized codon usage, introns, polyadenylation, and transcription termination sites. Methods of modifying nucleic acid constructs to increase expression levels in plants are also generally known in the art. See, e.g. Rogers et al., 260 J. BIOL. CHEM. 3731-38 (1985); Cornejo et al., 23 PLANT MOL. BIOL. 567-81 (1993).

In engineering a plant system to improve the rate of transcription of a protein, various factors known in the art may be used including regulatory sequences such as positively or negatively acting sequences, enhancers and silencers, as well as, chromatin structure. The present invention provides that at least one of these factors may be utilized in engineering plants to express a protein of interest.

Fragments: include any portion of an amino acid sequence which retains at least one structural or functional characteristic of the subject post-translational enzyme or heterologous polypeptide.

Functional equivalent: a protein or nucleic acid molecule that possesses functional or structural characteristics that are substantially similar to a heterologous protein, polypeptide, enzyme, or nucleic acid. A functional equivalent of a protein may contain modifications depending on the necessity of such modifications for the performance of a specific function. The term "functional equivalent" is intended to include the "fragments," "mutants," "hybrids," "variants," "analogs," or "chemical derivatives" of a molecule.

Fusion protein: a protein in which peptide sequences from different proteins are covalently linked together.

Holo-MIS: refers to the homodimer MIS precursor protein wherein each monomer comprises both the N-terminal pro-domain and 12.5 kD C-terminal region. Holo-MIS serves as the substrate for enzymatic activation, which releases the C-terminal fragment as a 25 kD homodimer that functions as the bioactive MIS cytokine.

hMIS: refers to a human recombinant MIS protein, peptide, or fragment thereof.

Introduction: insertion of a nucleic acid sequence into a cell, by methods including infection, transfection, transformation or transduction.

Isolated: as used herein, refers to any element or compound separated not only from other elements or compounds that are present in the natural source of the element or compound, but also from other elements or compounds and, as used herein, preferably refers to an element or compound found in the presence of (if anything) only a solvent, buffer, ion, or other component normally present in a solution of the same.

Müllerian Inhibiting Substance (MIS): is a protein belonging to the TGF-β gene family and is produced by the fetal testis as a 140 kDa glycosylated disulfide-linked homodimer that causes regression of the Müllerian duct in the male fetus. Under reducing conditions, the protein migrates on gel electrophoresis at an apparent molecular weight of 70 kDa. The protein can be proteolytically cleaved by exogenous plasmin into two distinct fragments that migrate electrophoretically as 57 kDa and 12.5 kDa moieties with cleavage at residue 427 of the intact 535 amino acid monomer. The molecule is also referred to as Anti-Mullarian Hormone (AMH).

Monocotyledon (monocot): a flowering plant whose embryos have one cotyledon or seed leaf. Examples of monocots include: lilies; grasses; corn; rice, grains including oats, wheat and barley; orchids; irises; onions and palms.

Operably linked: as used herein, refers to the state of any compound, including but not limited to deoxyribonucleic acid, when such compound is functionally linked to any promoter.

Plant culture medium: any combination of amino acids, salts, sugars, plant growth regulators, vitamins, and/or elements and compounds that will maintain and/or support the growth of any plant, plant cell, or plant tissue. A typical plant culture medium has been described by Murashige & Skoog, 15 PHYSIOL. PLANT. 473-97 (1962).

Plant host system: includes plants, including, but not limited to, monocots, dicots, and specifically maize, soybean, and tobacco modified for production of a heterologous protein. Plant host system also encompasses plant cells. Plant cells includes suspension cultures, embryos, meristematic regions, callus tissue, leaves, roots, shoots, gametophytes, sporophytes, pollen, seeds and microspores. Plant host systems may be at various stages of maturity and may be grown in liquid or solid culture, or in soil or suitable medium in pots, greenhouses or fields. Recombinant protein expression in plant host systems may be transient or permanent. Plant host system also refers to any clone of such a plant, seed, selfed or hybrid progeny, propagule whether generated sexually or asexually, and descendents of any of these, such as cuttings or seed cells inoculated with recombinant viruses modified to direct production of rec. Plant host system may also comprise plants or plant cells inoculated with recombinant viruses modified to direct production of recombinant protein within the plant cells.

Plant sample: a tissue, organ, or subset of the plant, selected to have the preferred accumulation level, quality, or storability for production of the desired protein.

Plant transfection: broadly refers to processes by which plants cells are modified by the presence of heterologous nucleic acids (e.g.,DNA or RNA delivered via viral or bacterial vectors or mechanical means such as gene gun, electroporation, or "whisker" technologies) that yields protein products but does not involve integration of the genetic elements into the plant host genome. See, e.g., U.S. Pat. Nos. 5,889,190, 5,977,438, and 5,316,931.

Plant transformation and cell culture: broadly refers to the processes by which plant cells are genetically altered and transferred to an appropriate plant culture medium for maintenance, further growth, and/or further development. Transformation of genetic elements results in the integration of the genetic elements into the plant host genome, which may be transmitted to the plant progeny through sexual or asexual reproduction.

Promoters: to produce the desired pattern or levels of protein expression in plants, the expression of the heterologous protein may be placed under the direction of a plant promoter.

Promoters suitable for use in accordance with the present invention are described in the art. See e.g., WO 91/198696. Examples of promoters that may be used in accordance with the present invention include non-constitutive promoters or constitutive promoters, such as, the nopaline synthetase and octopine synthetase promoters, cauliflower mosaic virus (CaMV) 19S and 35S promoters, and the figwort mosaic virus (FMV) 35S promoter. See U.S. Pat. No. 6,051,753.

In one aspect of the present invention, the recombinant hMIS may be expressed in a specific tissue, cell type, or under more precise environmental conditions or developmental control. Promoters directing expression in these instances are known as inducible promoters. In the case where a tissue-specific promoter is used, protein expression is particularly high in the tissue from which extraction of the protein is desired. Depending on the desired tissue, expression may be targeted to the endosperm, aleurone layer, embryo (or its parts as scutellum and cotyledons), pericarp, stem, leaves, tubers, roots, etc. Examples of known tissue-specific promoters include the tuber-directed class I patatin promoter, the promoters associated with potato tuber ADPGPP genes, the soybean promoter of beta-conglycinin (7S protein) which drives seed-directed transcription, and seed-directed promoters such as those from the zein genes of maize endosperm and rice glutelin-1 promoter. See, e.g., Bevan et al., 14 NUCLEIC ACIDS RES. 4625-38 (1986); Muller et al., 224 MOL. GEN. GENET. 136-46 (1990); Bray, 172 PLANTA 364-70 (1987); Pedersen et al., 29 CELL 1015-26 (1982); Russell & Fromm, 6 TRANSGENIC RES. 157-58 (1997).

Protein purification: broadly defined, any process by which proteins are separated from a mixture containing other elements or compounds on the basis of charge, molecular size or conformation, or binding affinity. Specific purification techniques known in the art that can be used include ion exchange chromatography, lectin affinity chromatography, immunoaffinity chromatography, reverse-phase chromatography and selective phase separation. See, e.g., MANIATIS ET AL., MOL. CLONING: A LAB. MANUAL (Cold Spring Harbor Laboratory, N.Y. 1989); AUSUBEL ET AL., CURRENT PROTOCOLS IN MOL. BIO. (Greene Publishing Associates and Wiley Interscience, N.Y. 1989); SCOPES, PROTEIN PURIFICATION: PRINCIPLES & PRACTICE (Springer-Verlag New York, Inc., NY 1994); U.S. Pat. Nos. 5,990,284, 5,804,694, and 6,037,456.

Reading frame: refers to the way (of three possible) of reading a sense nucleotide sequence as a series of triplets. Reading "in frame" means that the nucleotide triplets (codons) are translated into a nascent amino acid sequence of the desired recombinant protein.

Recombinant: as used herein, broadly describes various technologies whereby genes can be cloned, DNA can be sequenced, and protein products can be produced. As used herein, the term also describes proteins that have been produced following the transfer of genes into the cells of plant host systems.

Structural gene: a gene coding for a polypeptide that may be equipped with a suitable promoter, termination sequence and optionally other regulatory DNA sequences, and having a correct reading frame.

TGF-β (super) family; TGF-β proteins: refers to the proteins belonging to the Transforming Growth Factor-beta superfamily. This term broadly defines a class of proteins that are disulfide-linked homo- or heterodimers that are expressed as large precursor polypeptide chains containing a hydrophobic signal sequence, a long and relatively poorly conserved N-terminal pro region of several hundred amino acids, a cleavage site, and a mature domain comprising an N-terminal region which varies among the family members and a more highly conserved C-terminal region. In particular embodiment of the present invention, this C-terminal region, present in the processed mature proteins of all known family members, contains approximately 100 amino acids with a characteristic cysteine motif having a conserved six or seven cysteine skeleton. The position of the cleavage site between the mature and pro regions may vary among the family members, however, the cysteine pattern of the C-terminus of all of the proteins may be found to contain the identical format. Lechleider and Roberts, STRUCTURAL FEATURES OF THE TGF-βs in THE CYTOKINE NETWORK AND IMMUNE FUNCTIONS (Theze, ed., Oxford Univ. Press, N.Y. 1999).

Total secreted protein, secreted fraction: as used herein, refers to the protein recovered primarily from the extracelluar compartments of plant cells or tissues (either intact or shredded) by washing, submerging, or otherwise exposing tissues to appropriate buffers or solutions, by vacuum infiltration of solutions followed by centrifuagion, or by other methods that facilitate recovery of secreted proteins. Total secreted protein also refers to proteins recovered from the growth or porpagation medium of plants (e.g., hydroponically grown plants), plant cells (e.g., suspension cultured cells, protoplasts, calli), or plant tissues (e.g., organ cultures, hairy root cultures). The secreted protein or secreted fraction is a subset of total soluble proteins which are recovered from a homogenate of plants, tissues or cells.

Total soluble protein: total protein recovered in the aqueous fraction of the homogenate from a plant host system Transgene: an engineered gene comprising a promoter to direct gene expression, a 5' untranslated region to initiate translation, a protein coding region, and a polyadenylation/termination region to stop gene transcription. An intervening sequence (intron or IVS) may be included after the promoter, to potentially enhance expression. The protein coding region may include the desired protein to be produced, and possibly a signal peptide or fusion to an additional region(s) that allows protein targeting, stabilization, and/or purification.

Transgenic: a plant host system engineered to contain a novel, laboratory-designed transgene.

Transgenic plants: plant host systems that have been subjected to one or more methods of genetic transformation; plants that have been produced following the transfer of genes into the cells of plant host systems.

Variant: an amino acid sequence that is altered by one or more amino acids. The variant may have "conservative" changes, wherein a substituted amino acid has similar structural or chemical properties, e.g., replacement of leucine with isoleucine. More rarely, a variant may have "non-conservative" changes, e.g., replacement of a glycine with a tryptophan. Analogous minor variations may also include amino acid deletions or insertions, or both. Guidance in determining which amino acid residues may be substituted, inserted, or deleted may be found using computer programs well known in the art, for example, DNASTAR© software.

Plant Expression Vectors

Expression vectors useful in the present invention comprise a nucleic acid sequence encoding a hMIS expression cassette, designed for operation in plants, with companion sequences upstream and downstream from the expression cassette. The present invention envisions the nucleic acid sequence of the expression cassette to encode the full length hMIS protein or the biologically active C-terminal region of hMIS. The companion sequences may be of plasmid or viral origin and provide necessary characteristics to the vector to permit the vectors to be generated in bacteria and then introduced to the desired plant host system. A cloning vector of this invention is designed so that a coding nucleic acid sequence inserted at a particular site will be transcribed and translated. A typical expression vector may contain a promoter, selection marker, nucleic acids encoding signal sequences, and regulatory sequences, e.g., polyadenylation sites, 5'-untranslated regions, and 3'-untranslated regions, termination sites, and enhancers. "Vectors" include viral derived vectors, bacterial derived vectors, plant derived vectors and insect derived vectors.

The basic bacterial/plant vector construct may preferably comprise a broad host range prokaryote replication origin; a prokaryote selectable marker; and, for *Agrobacterium* transformations, T-DNA sequences for *Agrobacterium*-mediated transfer to plant chromosomes. Where the hMIS gene is not readily amenable to detection, the construct will preferably also have a selectable marker gene suitable for determining if a plant cell has been transformed. A general review of suitable markers for the members of the grass family is found in Wilmink & Dons, 11(2) PLANT MOL. BIOL. REPTR. 165-85 (1993).

Sequences suitable for permitting integration of the heterologous sequences into the plant genome may be used as well. These might include transposon sequences, and the like, Cre/ lox sequences and host genome fragments for homologous recombination, as well as Ti sequences which permit random insertion of a hMIS expression cassette into a plant genome.

Suitable prokaryote selectable markers, useful for preparation of plant expression cassettes, include resistance toward antibiotics such as ampicillin, tetracycline, or kanamycin. Other DNA sequences encoding additional functions may also be present in the vector, as is known in the art. Usually, the plant selectable marker gene will encode antibiotic resistance, with suitable genes including at least one set of genes coding for resistance to the antibiotic spectinomycin, the streptomycin phosphotransferase (spt) gene coding for streptomycin resistance, the neomycin phosphotransferase (nptII) gene encoding kanamycin or geneticin resistance, the hygromycin phosphotransferase (hpt or aphiv) gene encoding resistance to hygromycin, acetolactate synthase (als) genes and modifications encoding resistance to, in particular, the sulfonylurea-type herbicides, genes coding for resistance to herbicides which act to inhibit the action of glutamine synthase such as phosphinothricin or basta (e.g., the bar gene), or other similar genes known in the art.

The constructs of the subject invention will include the expression vector for expression of full length hMIS or the biologically active C-terminal region of hMIS. Generally, there will be at least one expression cassette, and two or more are feasible, including a selection cassette. The recombinant expression vector contains, in addition to the nucleic acid sequence encoding hMIS, at least one of the following elements: a promoter region, signal sequence, 5' untranslated sequences, initiation codon depending upon whether or not the hMIS structural gene comes equipped with one, and transcription and translation termination sequences.

In a preferred aspect of the present invention, a gene encoding full length hMIS or the C-terminal region of hMIS is inserted into an appropriate expression vector, i.e., a vector which contains the necessary elements for the transcription and translation of the inserted coding sequence, or in the case of an RNA viral vector, the necessary elements for replication and translation. Methods for providing transgenic plants of the present invention include constructing expression vectors containing a protein coding sequence, and/or an appropriate signal peptide coding sequence, and appropriate transcriptional/translational control signals. These methods include in vitro recombinant DNA techniques, synthetic techniques and in vivo recombination/genetic recombination. See, e.g., TRANSGENIC PLANTS: PROD. SYS. FOR INDUS. & PHARM. PROTEINS (Owen & Pen eds., John Wiley & Sons, 1996); GALUN & BREIMAN DES, TRANSGENIC PLANTS (Imperial College Press, 1997); APPLIED PLANT BIOTECH. (Chopra, Malik, & Bhat eds., Sci. Pubs., Inc., 1999); U.S. Pat. Nos. 5,620,882; 5,959,177; 5,639,947; 5,202,422; 4,956,282; WO 98/10062; WO 97/38710.

Signal Sequence

Also included in chimeric genes used in the practice of the methods of the present invention are signal sequences. In addition to encoding full length hMIS or the C-terminal region of hMIS, the chimeric gene also encodes a signal peptide that allows processing and translocation of the protein, as appropriate. The signal sequences may be derived from mammals, or from plants such as wheat, barley, cotton, rice, soy, and potato. These signal sequences will direct full length hMIS or the C-terminal region of hMIS to a subcellular location (e.g., cytosol, endoplasmic reticulum, apoplast, plastid, and chloroplast) within the plant host system. This may result in increased accumulation and easier purification of hMIS. The signal peptides contemplated by the present invention include the patatin signal derived from the potato gene encoding the storage protein patatin. This signal peptide directs targeting of fused polypeptides into the plant endoplasmic reticulum (ER) where the signal peptide is precisely cleaved to generate a mature protein or pro-protein. In the absence of additional signals for ER or Golgi retention or vacuolar targeting, proteins delivered into the ER in plants are routed through the endomembrane system and secreted into the extracellular space (apoplast).

Those of skill can routinely identify new signal peptides. For example, plant secretory signal peptides typically have a tripartite structure, with positively-charged amino acids at the N-terminal end, followed by a hydrophobic region and then the cleavage site within a region of reduced hydrophobicity. Although sequence homology is not always present in the signal peptides, hydrophilicity plots demonstrate that the signal peptides of these genes are relatively hydrophobic. See generally, STRYER, BIOCHEM. 768-70 (3rd ed., W.H. Freeman & Co., N.Y., 1988). The conservation of this mechanism is demonstrated by the fact that cereal α-amylase signal peptides are recognized and cleaved in foreign hosts such as E. coli and S. cerevisiae, however particular signal sequences may allow higher expression in some hosts.

The flexibility of this mechanism is reflected in the wide range of polypeptide sequences that can serve as signal peptides. Thus, the ability of a sequence to function as a signal peptide may not be evident from casual inspection of the amino acid sequence. Methods designed to predict signal peptide cleavage sites identify the correct site for only about 75% of the sequences analyzed. See HEIJNE, CLEAVAGE-SITE MOTIFS IN PROTEIN TARGETING SEQUENCES, in 14 GENETIC ENG'G (Setlow ed., Plenum Press, N.Y. 1992).

Transcription and Translation Terminators

The expression vectors of the present invention typically have a transcriptional termination region at the opposite end of the gene from the transcription initiation regulatory region. The transcriptional termination region may normally be associated with the transcriptional initiation region or derived from a different gene. The transcriptional termination region to be used may be selected, particularly for stability of the mRNA, to enhance expression. Illustrative transcriptional termination regions include the NOS terminator from Agrobacterium Ti plasmid and the rice α-amylase terminator.

The transcription termination process also may provide signals for the addition of polyadenylation tails added to the gene transcription product. Alber & Kawasaki, 1 MOL. & APPL. GENETICS 419-34 (1982). Polyadenylation signal sequences include but are not limited to those defined in the Agrobacterium octopine synthetase signal, (Gielen, et al., 3 EMBO J. 835-46 (1984)), or the nopaline synthase of the same species (Depicker, et al., 1 MOL. APPL. GENETICS 561-73 (1982)).

Nucleic Acids

In accordance with the invention, polynucleotide sequences (e.g., cDNA or genomic sequences) which encode the holo hMIS or the C-terminal region of hMIS (or other TGF-β proteins or bioactive fragments) may be used to generate recombinant nucleic acid sequences that direct the expression of such proteins, or functional equivalents thereof, in plant cells.

It will be appreciated by those skilled in the art that, as a result of the degeneracy of the genetic code, a multitude of polynucleotide sequences may be produced which encode the full length hMIS or the C-terminal region of hMIS (or other TGF-β proteins), some bearing minimal homology to the nucleotide sequences of any known and naturally occurring gene. Thus, the invention contemplates each and every possible variation of nucleotide sequence that could be made by selecting combinations based on possible codon choices. These combinations are made in accordance with the standard triplet genetic code.

Altered DNA sequences which may be used in accordance with the invention include deletions, additions or substitutions of different nucleotide residues resulting in a sequence that encodes the same or a functionally equivalent gene product. The gene product itself may contain deletions, additions or substitutions of amino acid residues within a protein sequence, which result in a functionally equivalent protein. Altered nucleic acid sequences include nucleic acid sequences encoding full length hMIS or the C-terminal region of hMIS, or functional equivalent thereof, including those sequences with deletions, insertions, or substitutions of different nucleotides resulting in a polynucleotide that encodes the same or a functionally equivalent hMIS. Included within this definition are polymorphisms which may or may not be readily detectable using a particular oligonucleotide probe of the polynucleotide encoding hMIS and improper or unexpected hybridization to alleles, with a locus other than the normal chromosomal locus for the polynucleotide sequence hMIS. The encoded protein may also be "altered" and contain deletions, insertions, or substitutions of amino acid residues which produce a silent change and result in a functionally equivalent hMIS. Deliberate amino acid substitutions may be made on the basis of similarity in polarity, charge, solubility, hydrophobicity, hydrophilicity, and/or the amphipathic nature of the residues as long as the biological or immunological activity of full length hMIS or C-terminal hMIS is retained. For example, negatively charged amino acids include aspartic acid and glutamic acid; positively charged amino acids include lysine and arginine; and amino acids with uncharged polar head groups having similar hydrophilicity values include leucine, isoleucine, and valine; glycine and alanine; asparagine and glutamine; serine and threonine; and phenylalanine and tyrosine.

The nucleic acid sequences of the invention may be engineered in order to alter the coding sequence for a variety of ends including, but not limited to, alterations that modify expression and processing of the gene product. For example, alternative secretory signals may be substituted for or used in addition to the native secretory signal. See, e.g., U.S. Pat. No. 5,716,802. Additional mutations may be introduced using techniques which are well known in the art, e.g., site-directed mutagenesis, to insert new restriction sites, or alter glycosylation or phosphorylation patterns.

Additionally, when being expressed in non-human cells, the polynucleotides encoding full length hMIS or the C-terminal region of hMIS may be modified in the silent position of any triplet amino acid codon so as to better conform to the codon preference of the particular host organism. More specifically, the efficiency of translating a protein in a given host organism can be regulated through codon bias, meaning that the available 61 codons for a total of 20 amino acids are not evenly used in translation, an observation that has been made for prokaryotes (Kane, 6 CURRENT Op. BIOTECH. 494-500 (1995)), and eukaryotes (ERNST, CODON USAGE & GENE EXPRESSION 196-99 (Elsevier Pub., Cambridge 1988). An application of these observations, i.e., the adaptation of the codon bias of a bacterial gene to the codon bias of a higher plant, resulted in significantly higher accumulation of the foreign protein in the plant. Perlak et al., 88(8) P.N.A.S. 3324-28 (1991); see also Murray et al., 17 NUCL. ACIDS RES. 477-98 (1989); U.S. Pat. No. 6,121,014. Codon usage tables have been established not only for organisms, but also for organelles and specific tissues (Kazusa DNA Research Inst., see website <kazusa.orjp>), and their general availability enables researchers to adopt the codon usage of a given gene to the host organism. Other factors, for example, the context of the initiator methionine start codon (Kozak, 234 GENE 187-208 (1999)), may influence the translation rate for a given protein in a host organism, and may therefore be taken into consideration to enhance translation. See also Taylor et al., 210 MOL. GENETICS 572-77 (1987). Translation may also be optimized by reference to codon sequences that may generate signals for intron splicing (PLANT MOL. BIO. LABFAX (Croy, ed. 1993)), mRNA instability and polyadenylation (Perlak et al., supra).

The nucleic acid sequences of the invention also may include sequences that encode variants of the described hMIS. These amino acid sequence variants of hMIS may be prepared by methods known in the art by introducing appropriate nucleotide changes into an authentic or variant hMIS encoding polynucleotide. There are two variables in the construction of amino acid sequence variants: the location of the mutation and the nature of the mutation. The amino acid sequence variants are preferably constructed by mutating the polynucleotide to give an amino acid sequence that does not occur in nature. These amino acid alterations can be made at sites that differ, from different species (variable positions) or in highly conserved regions (constant regions). Sites at such locations will typically be modified in series, e.g., by substituting first with conservative choices (e.g., hydrophobic amino acid to a different hydrophobic amino acid) and then with more distant choices (e.g., hydrophobic amino acid to a charged amino acid), and then deletions or insertions may be made at the target site.

Amino acids are divided into groups based on the properties of their side chains (polarity, charge, solubility, hydrophobicity, hydrophilicity, and/or the amphipathic nature): (1) hydrophobic (leu, met, ala, ile); (2) neutral hydrophobic (cys, ser, thr); (3) acidic (asp, glu); (4) weakly basic (asn, gln, his); (5) strongly basic (lys, arg); (6) residues that influence chain orientation (gly, pro); and (7) aromatic (trp, tyr, phe). Conservative changes encompass variants of an amino acid position that are within the same group as the native amino acid. Moderately conservative changes encompass variants of an amino acid position that are in a group that is closely related to the native amino acid (e.g., neutral hydrophobic to weakly basic). Non-conservative changes encompass variants of an amino acid position that are in a group that is distantly related to the "native" amino acid (e.g., hydrophobic to strongly basic or acidic).

Amino acid sequence deletions generally may range from about 1 to 30 residues, preferably about 1 to 10 residues, and are typically contiguous. Amino acid insertions include amino- and/or carboxyl-terminal fusions ranging in length from one to one hundred or more residues, as well as intrasequence insertions of single or multiple amino acid residues. Intrasequence insertions may range generally from about 1 to 10 amino residues, preferably from 1 to 5 residues. Examples of terminal insertions include the heterologous signal sequences necessary for secretion or for intracellular targeting in different host cells.

In one method, polynucleotides encoding a protein are changed via site-directed mutagenesis. This method uses oligonucleotide sequences that encode the polynucleotide sequence of the desired amino acid variant, as well as a sufficient adjacent nucleotide on both sides of the changed amino acid to form a stable duplex on either side of the site of being changed. In general, the techniques of site-directed mutagenesis are well known to those of skill in the art and this technique is exemplified by publications such as, Adelman et al., 2 DNA 183-93 (1983). A versatile and efficient method for producing site-specific changes in a polynucleotide sequence was published by Zoller & Smith, 10 NUCLEIC ACIDS RES. 6487-500 (1982).

Mutations may also provide one or more unique restriction sites that do not alter the amino acid sequence encoded by the nucleic acid molecule, but merely provide unique restriction sites useful for manipulation of the molecule. Thus, the modified molecule could be made up of a number of discrete regions, or D-regions, flanked by unique restriction sites. These discrete regions of the molecule are herein referred to as cassettes. Molecules formed from multiple copies of a cassette are another variant of the present gene which is encompassed by the present invention. Recombinant or mutant nucleic acid molecules or cassettes which provide desired characteristics such as resistance to endogenous enzymes such as collagenase are also encompassed by the present invention.

PCR may also be used to create amino acid sequence variants of a recombinant protein. When small amounts of template DNA are used as starting material, a primer(s) that differs slightly in sequence from the corresponding region in the template DNA can generate the desired amino acid variant. PCR amplification results in a population of product DNA fragments that differ from the polynucleotide template encoding the protein at the position specified by the primer. The product DNA fragments replace the corresponding region in the plasmid and this gives the desired amino acid variant.

A further technique for generating amino acid variants is the cassette mutagenesis technique described in Wells et al., 34 GENE 315 (1985); and other mutagenesis techniques well known in the art, such as, for example, the techniques in Sambrook et al., supra; Ausubel et al., CURRENT PROTOCOLS IN MOL. BIOL. supra.

Due to the inherent degeneracy of the genetic code, other DNA sequences which encode substantially the same or a functionally equivalent amino acid sequence or polypeptide, specifically, comprising a consistent (Gly-X-Y), amino acid structure, that are natural, synthetic, semi-synthetic, or -recombinant, may be used in the practice of the claimed invention. Such DNA sequences may include those which are capable of hybridizing to the appropriate protein sequence under stringent conditions.

Thus, the invention further relates to nucleic acid sequences that hybridize to the above-described sequences. In particular, the invention relates to nucleic acid sequences that hybridize under stringent conditions to the above-described nucleic acids. As used herein, the terms "stringent conditions" and "stringent hybridization conditions" mean that hybridization will generally occur if there is at least 95% and preferably at least 97% identity between the sequences. An example of stringent hybridization conditions is overnight incubation at 42° C. in a solution comprising 50% formamide, 5×SSC (150 mM NaCl, 15 mM trisodium citrate), 50 mM sodium phosphate (pH 7.6), 5× Denhardt's solution, 10% dextran sulfate, and 20 micrograms/milliliter denatured, sheared salmon sperm DNA, followed by washing the hybridization support in 0.1×SSC at approximately 65° C. Other hybridization and wash conditions are well known and are exemplified in SAMBROOK, ET AL., MOLECULAR CLONING: A LABORATORY MANUAL (2d ed., Cold Spring Harbor, N.Y. (1989)), particularly Chapter 11.

Transformation of Plant Cells

Transformation is a process by which exogenous DNA enters and changes a recipient cell. It may occur by natural or artificial processes by using various methods well known in the art. Transformation may rely on any known method for the insertion of foreign nucleic acid sequences into a prokaryotic or eukaryotic host cell. The method of choice is selected based on the type of host cell being transformed and may include, but is not limited to, viral infection, electroporation, heat shock, lipofection, A. tumefaciens-mediated transfection, and particle bombardment.

Expression vectors may be introduced into the plant host system with Agrobacterium tumefaciens. Horsch et al., 227 SCIENCE 1229 (1985). Description of Agrobacterium vector systems and methods for Agrobacterium-mediated gene transfer are provided by Gruber et al., VECTORS FOR PLANT TRANSFORMATION, Glick et al., (eds.), 89-119 (CRC Press, 1993), and Moloney et al., 8 PLANT CELL REPORTS 238 (1989).

More specifically, standard methods for the transformation of rice, wheat, corn, sorghum, and barley are described in the art. See Christou et al., 10 TRENDS IN BIOTECH. 239 (1992); Lee et al., 88 P.N.A.S. 6389-93 (1991). Wheat can be transformed by techniques similar to those employed for transforming corn or rice. Furthermore, Casas et al., 90 P.N.A.S. 11212-16 (1993), describe a method for transforming sorghum, while Lazzeri, 49 METHODS MOL. BIOL. 95-106 (1995), teach a method for transforming barley. Suitable methods for corn transformation are provided by Fromm et al., 8 BIO/TECHNOLOGY 833-39 (1990); Gordon-Kamm et al., 2 PLANT CELL 603-18 (1990); Russell et al., 6 TRANSGENIC RES., 157-58 (1997); U.S. Pat. No. 5,780,708.

Vectors useful in the practice of the present invention may be microinjected directly into plant cells by use of micropipettes to mechanically transfer the recombinant DNA. Crossway, 202 MOL. GEN. GENET., 179-85 (1985). The genetic material may also be transferred into the plant cell by using polyethylene glycol, Krens et al., 96 NATURE 72-74 (1982).

Another method of introduction of nucleic acid segments is high velocity ballistic penetration by small particles with the nucleic acid either within the matrix of small beads or particles, or on the surface. Klein et al., 327 NATURE 70-73 (1987); Knudsen & Muller, 185 PLANTA 330-36 (1991).

Additionally, another method of introduction would be fusion of protoplasts with other entities, either minicells, cells, lysosomes or other fusible lipid-surfaced bodies, Fraley et al., 79 P.N.A.S. 1859-63 (1982).

The vector may also be introduced into the plant cells by electroporation. (Fromm et al., 82 P.N.A.S. 5824-28 (1985). In this technique, plant protoplasts are electroporated in the presence of plasmids containing the gene construct. Electrical impulses of high field strength reversibly permeabilize biomembranes allowing the introduction of the plasmids. Electroporated plant protoplasts can reform a cell wall, divide, and form plant callus. See U.S. Pat. No. 5,584,807.

Isolating Progeny Containing the Expressed Protein of Interest

Progeny containing the desired protein can be identified by assaying for the presence of the heterologous protein using assay methods well known in the art. Such methods include Western blotting, immunoassays, binding assays, enzyme activity assays and any assay designed to detect a biologically functional heterologous protein. See, for example, the assays described in KLEIN, IMMUNOLOGY: SCI OF SELF-NONSELF DISCRIMINATION (John Wiley & Sons eds., New York, N.Y. 1982).

Preferred screening assays detect the biological activity of the hMIS. These assays identify, for example, the production of a complex, formation of a catalytic reaction product, the release or uptake of energy, cell growth, identification as authentic by the appropriate antibody, and the like. For example, a progeny containing a hMIS molecule produced by this method may be recognized by an antibody to binds to an authentic antigenic site on the protein in a standard immunoassay such as an ELISA or other immunoassays known in the art. See ANTIBODIES: A LAB. MANUAL (Harlow & Lane, eds., Cold Spring Harbor Laboratory, Cold Spring Harbor, N.Y. 1988).

Plant Regeneration

Plant regeneration from cultured protoplasts is described in EVANS, ET AL., HANDBOOK OF PLANT CELL CULTURES, Vol. 1: (Mac-Millan Publishing Co. New York 1983); CELL CULTURE & SOMATIC CELL GENETICS OF PLANTS, (Vasil I. R., ed., Acad. Press, Orlando, Vol. 11984, and Vol. III 1986).

All plants from which protoplasts can be isolated and cultured to give whole regenerated plants may be transformed by the present invention so that whole plants are recovered which contain the transferred gene. It is known that virtually all plants can be regenerated from cultured cells or tissues, including but not limited to all major species of sugarcane, sugar beet, cotton, fruit and other trees, legumes and vegetables, dicots, and monocots.

Methods for regeneration vary from species to species, but generally a cell capable of being cultured either alone or as part of a tissue and containing copies of the heterologous protein gene is first isolated. Callus tissue may be grown from this cell and shoots may be induced to develop from the callus and subsequently rooted, or shoots may be initiated directly from a cell within a meristem.

Alternatively, embryo formation can be induced to develop in the cell suspension. These embryos have the capacity to germinate to form plants. The culture media will generally contain various amino acids and hormones, such as auxin and cytokinins. It is also advantageous to add glutamic acid and proline to the medium, especially for such species as corn and alfalfa. Shoots and roots normally develop simultaneously. Efficient regeneration will depend on the medium, on the genotype, and on the history of the culture. If these three variables are optimized, then regeneration may be fully reproducible and repeatable.

A plant of the present invention containing the expression vector comprised of a first nucleic acid sequence that is capable of regulating the transcription of a second nucleic acid sequence encoding a significant portion of a peptide that is capable of targeting a protein to a sub-cellular location and fused to this second nucleic acid, a third nucleic acid encoding the full length hMIS or the C-terminal region of hMIS, is cultivated using methods well known to one skilled in the art. Any of the transgenic plants of the present invention may be cultivated to isolate the desired protein they contain.

After cultivation, the transgenic plant is harvested to recover or express the full length hMIS or the C-terminal region of hMIS. This harvesting step may consist of harvesting the entire plant, or only the leaves, or roots of the plant. This step may either kill the plant or if only the portion of the transgenic plant is harvested may allow the remainder of the plant to continue to grow.

The transgenic plants according to this invention can also be used to develop hybrids or novel varieties embodying the desired traits. Such plants would be developed using traditional selection type breeding.

The mature plants, grown from the transformed plant cells are selfed and the resulting homozygous transgenic plants are identified. Alternatively, an outcross can be performed, to move the gene into another plant. In either case, the transgenic plants produce seed containing the proteins of the present invention. The transgenic plants according to this invention can be used to develop hybrids or novel varieties embodying the desired traits. Such plants would be developed using traditional selection type breeding.

The following examples will illustrate the invention in greater detail, although it will be understood that the invention is not limited to these specific examples. Various other examples will be apparent to the person skilled in the art after reading the present disclosure without departing from the spirit and scope of the invention. It is intended that all such other examples be included within the scope of the appended claims.

EXAMPLES

Without further elaboration, it is believed that one skilled in the art, using the preceding description, can utilize the present invention to the fullest extent. The following examples are illustrative only, and not limiting of the remainder of the disclosure in any way whatsoever. The following techniques can be adapted by one skilled in the art to produce, in any appropriate plant host system, a protein of the TGF-β superfamily.

Example 1

Production of holo-hMIS in Transgenic Tobacco Plants

Figure 3:
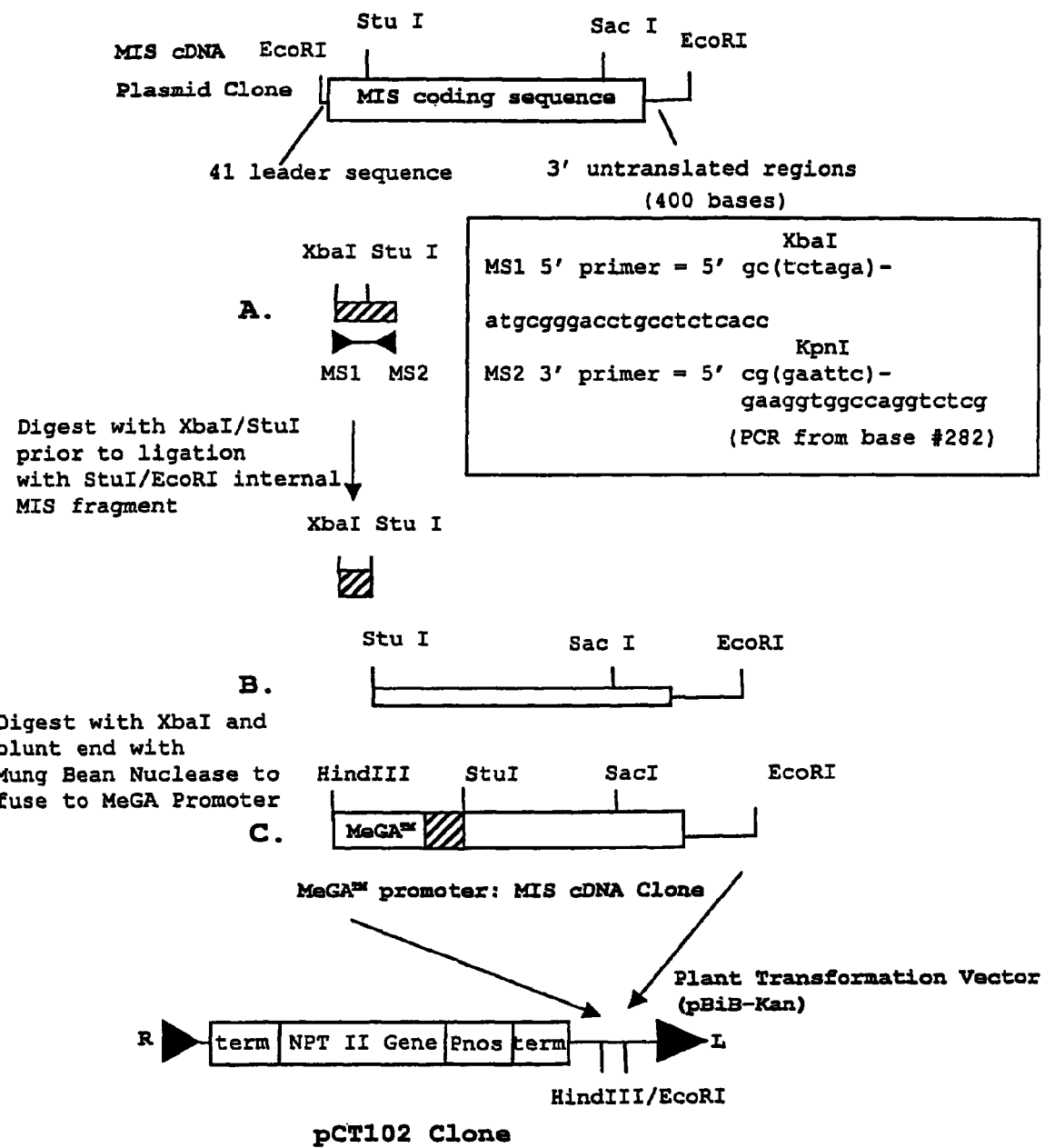

Construction of a Vector for Expression of Holo-hMIS in Transgenic Tobacco Plants The coding region of the full-length MIS was derived from a cDNA clone of human MIS with the sequence described in GenBank Accession #K03474 (FIG. 2). The MIS cDNA sequence was present as a 2.0 kb EcoRI fragment in pBluescript II (KS) (pBS II; Stratagene). The general cloning strategy is illustrated in FIG. 3. In order to eliminate unwanted 5' leader sequences and provide a flanking XbaI site, the first 282 by of the full-length MIS coding region was PCR amplified using MS1 and MS2 primers (FIG. 3). The PCR product was digested with XbaI and StuI and ligated to the full-length MIS vector digested with StuI. The ligation product was digested with XbaI and EcoRI and the 2.0 kb fragment was cloned into pBS II vector. A plasmid containing the wound-inducible MEGA promoter (an MGA-inducible plant promoter) was digested with EcoRI and the ends were blunted with Mung Bean Nuclease. The plasmid was subsequently digested with HindIII to excise the promoter fragment as a HindIII/blunt-end fragment. The modified full-length MIS clone was digested with XbaI and blunted with Mung Bean Nuclease and ligated to the HindIII/blunt-end MEGA promoter (an MGA-inducible plant promoter) fragment. The MEGA promoter (an MGA-inducible plant promoter):MIS junction was confirmed by sequence analysis (FIG. 4). The resulting 2.3 kb HindIII/EcoRI fragment was cloned into the HindIII/EcoRI site of pRiB-Kan plant transformation vector. The transgenic plants resulting from transformation using this vector were designated CT102.

Transformation of Full-length hMIS Into Tobacco Plants.

The expression construct containing the MeGA.TM. promoter:MIS gene was introduced into tobacco leaf disks by Agrobacterium-mediated transformation. Horsch et al., 223 SCIENCE 496-498 (1984). First, small leaf disks were excised from axenically-grown tobacco seedlings (Nicotiana tabacum, cultivar Xanthi), dipped into a suspension of Agrobacterium tumefaciens containing the MEGA promoter (an MGA-inducible plant promoter):MIS transformation vector, co-cultivated for 24 hours, and transferred to medium which selected against growth of the bacteria (carbenicillin) and non-transformed plant cells (kanamycin). The transformed plant-cells were kanamycin resistant based on co-introduction of an NPTII gene. After 3-4 weeks of growth and development, differentiated shoots were excised and transferred to root-initiation medium. Following root development (usually 5-7 days), the plantlet was transferred to soil. Transgenic plants were transferred to the greenhouse within 10 weeks of initial transformation. At about 8 weeks, initial leaf tissue was excised, induced and screened by immuno dot-blotting for holo-hMIS expression. After several additional weeks of growth, leaf tissues were harvested for DNA, RNA and protein analyses as described below.

Figure 5:
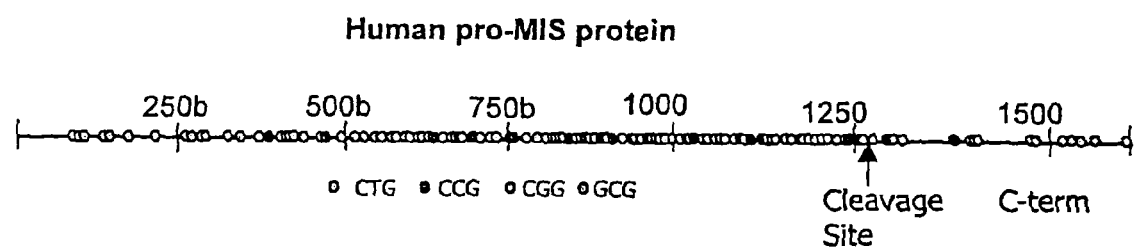

The transformation yielded 275 independent transgenic plants. The plants were screened for expression of MIS by RNA dot-blot Northerns. Briefly, excised leaf material was wound-induced by shredding into 1.5 mm strips, incubated at room temperature for various periods (e.g., 0, 4, 8 12 hr), and used for isolation of total RNA. The full-length human MIS cDNA was labeled and used as the hybridization probe for Northern slot-blot analyses. The majority of the plants showed little to no expression of the MIS mRNA. Southern analyses of selected plants showed that the plants contained 1 to 3 copies of the transgene. The CT102-0018 line had a moderate level of MIS mRNA and was used for further characterization of tobacco-synthesized holo-hMIS. The low frequency of transgenic plants showing significant MIS transgene expression was unusual based on previous experience of MEGA-driven human transgenes expressed in tobacco. The reduction in expression may reflect a codon usage in the hMIS gene that is problematic for tobacco (FIG. 5). It is contemplated that codon optimization of the MIS sequence to reflect tobacco codon preferences would significantly enhance production levels of the holo-MIS in tobacco.

Induction and Characterization of Expression of Holo-hMIS in Transgenic Plants.

In order to induce bioproduction of MIS, two grams of transgenic MIS plant tissue from CT102-0018 were wound-induced by shredding into 1.5 mm strips using an angel-hair pasta maker and incubated at room temperature for 24, 38, 72 and 92 hours. The MIS protein has a characteristic of moving through the endomembrane system slowly compared to other secreted proteins. For example, MIS protein synthesized in CHO cells is not detected in the media until 72 hours post-infection. The maximum accumulation of MIS mRNA in wound-induced transgenic plants was seen at 12 hours post-wounding, which is typical of transgenes driven by the MEGA promoter (an MGA-inducible plant promoter). However, the transgenic MIS protein was detected in the secreted fraction 58-72 hrs post-wound induction of the plant tissue.

Figure 6A:
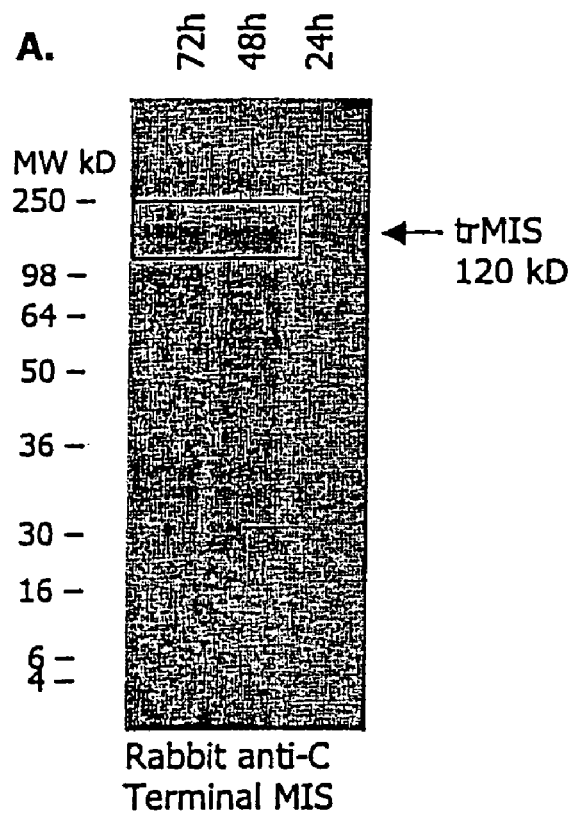
Figure 6B:
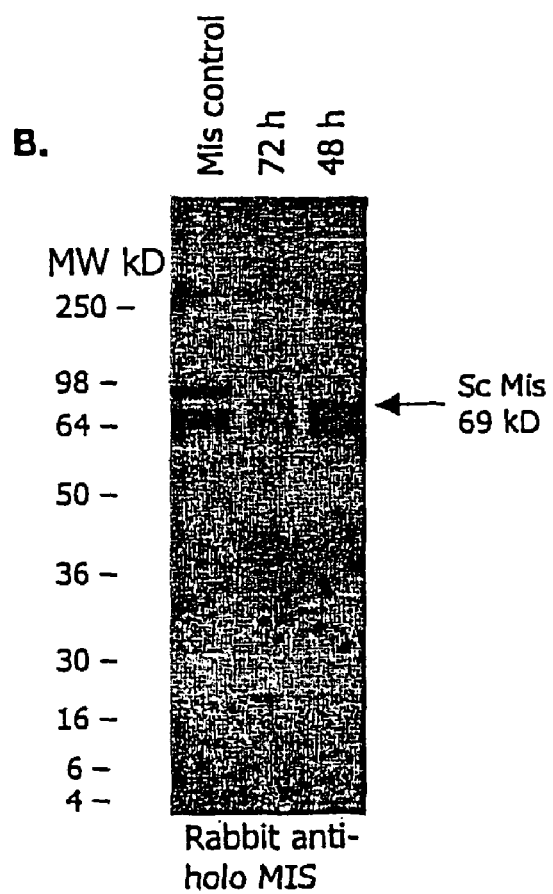

To extract total proteins, the tissue was ground to a fine powder in liquid nitrogen and homogenized in sample buffer (Laemmli, supra). The homogenate was centrifuged at 18,600 rpm for 20 min. The supernatant was collected and levels of total soluble protein were determined. Total protein samples (20 µg per lane) were analyzed on 10-20% SDS-PAGE (Laemmli, supra). Proteins were transferred to nitrocellulose membranes (0.22 µm Optitran, Schleicher & Schuell) according to the manufacturers' recommendation using a Criterion Blotter apparatus (BioRad) (see Current Protocols in Immunology). Western analysis was performed using rabbit polyclonal antibody raised against purified C-terminal MIS protein. As shown in FIG. 6 (panel A), bands at 120-130 kD were found to cross-react with the anti-C terminal MIS. The MIS protein represented approximately 0.005% of the total soluble protein present in the sample. To determine if the 120 kD cross-reacting band in panel A consisted of a homodimer of MIS, 20 µg of total protein from 48 and 72 hr induced material were analyzed on 10-20% SDS-PAGE gel, and the gel region covering 98 to 250 kD based on molecular weight standards was dissected and the proteins recovered by crushing and soaking the gel in reducing sample buffer (10% glycerol, 2.3% SDS, 62.5 mM Tris-HCl pH 6.8, 120 mM DTT). The samples were heated at 100° C. for 10 min prior to being loaded onto a 10-20% PAGE. As shown in FIG. 6 (panel B), Western analysis was performed using polyclonal anti-holo-MIS. Tobacco-synthesized proteins of 69 and 66 kD cross reacted with the anti-holo-MIS. The recombinant MIS from transgenic plants migrated with a slightly faster mobility than the CHO-derived holo-MIS control. These results clearly show that transgenic plants are able to produce holo-MIS as a disulfide linked homodimer. The predicted molecular weight based on amino acid composition of MIS is 56.7 kD. The differences in molecular size between the CHO-derived MIS and plant-derived MIS are likely due to differences in glycan composition (Cabanes-Macheteau et al., supra; Chrispeels and Faye, supra).

Holo-MIS is purified and subjected to further characterization. The plant derived holo-MIS is shown to have equivalent size to CHO-derived holo-MIS by analyzing the deglycosylated holo-MIS. Furthermore, the enzymatic release of the 25 kD homo-dimer C-terminal fragment from holo-MIS is demonstrated via plasmin digestion of the holo-MIS. Finally, the bioactivity of the C-terminal MIS, which is enzymatically cleaved from the holo-MIS is assayed.

Example 2

Production of Bioactive C-Terminal hMIS in Transgenic Tobacco Plants

Figure 7:
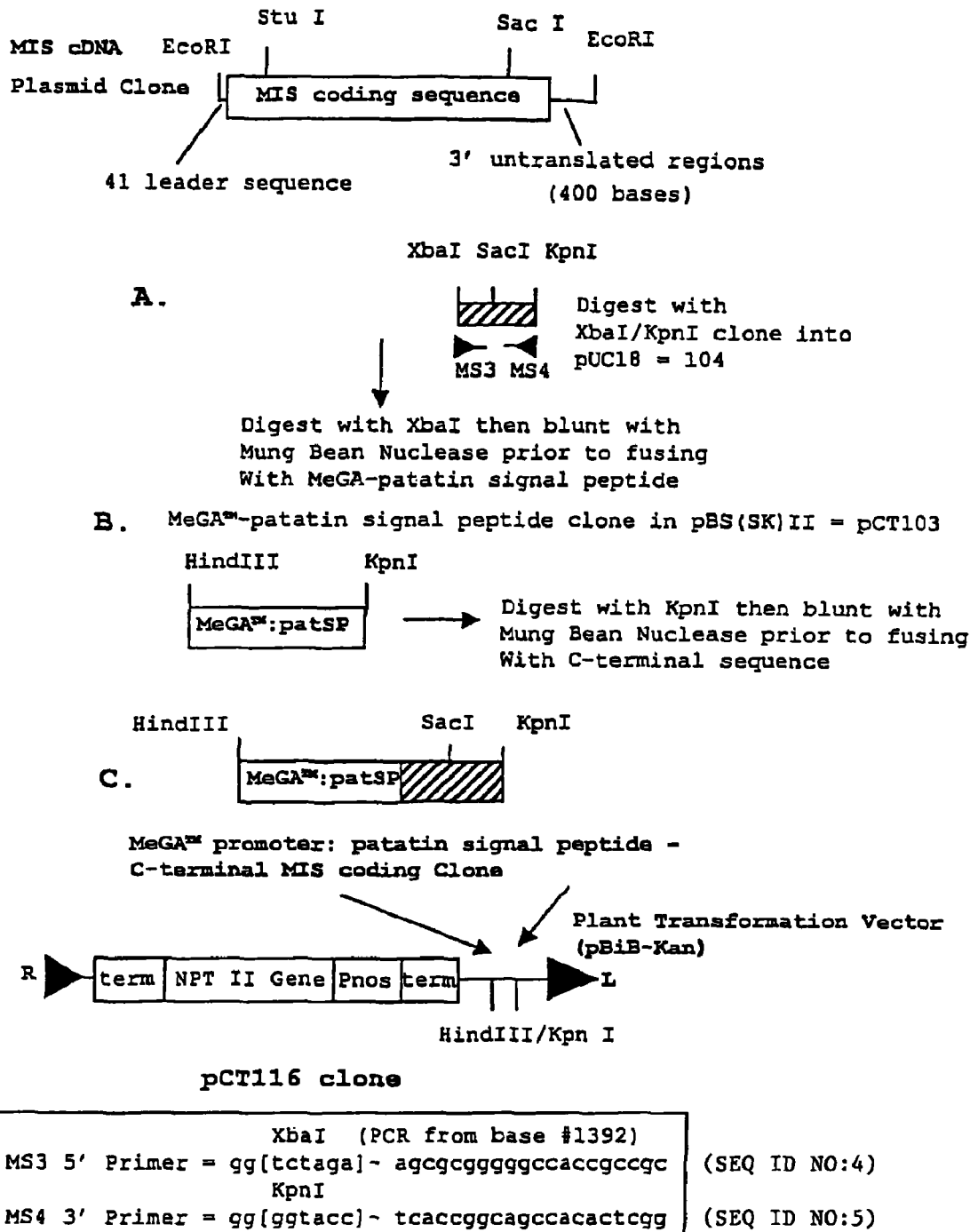

Construction of a Vector for Expression of C-terminal hMIS in Transgenic Tobacco Plants The MIS bioactive peptide is produced by a furin-like cleavage between amino acids ARG.sub.427 and SER.sub.428 of the mature holo-MIS precursor. The resulting 25 kD homo-dimer, C-terminal MIS, is the bioactive protein recognized by the MIS receptor protein. The natural bioactive C-terminal MIS is unglycosylated, obviating any need to modify plant-specific glycosylation to produce a human equivalent molecule. In order to produce the C-terminal MIS directly, it was necessary to provide a start codon and sequences encoding an in-frame signal peptide to direct the C-terminal MIS product into the endomembrane system for dimerization and secretion. To generate constructs for expression of the C-terminal bioactive MIS fragment in plants, the cDNA region encoding the C-terminus of human MIS [GenBank Accession #K03474 (FIG. 2)] was PCR-amplified and fused to sequences encoding a plant signal peptide derived from the potato patatin gene. The general cloning strategy is illustrated in FIG. 7. Based on the K03474 amino acid sequence, primers were designed and used to amplify the region encoding the C-terminal 99 amino acids of human MIS (FIG. 8). The primers were designed to provide flanking XbaI and KpnI restriction sites. The resulting PCR product was cloned into pUC18, sequence confirmed, and the resulting plasmid was designated pCT104. The plasmid pCT103, which contains a region comprising the MEGA promoter (an MGA-inducible plant promoter) operationally fused to sequences encoding the patatin signal peptide (patatin SP; FIG. 9), was digested with KpnI and treated with Mung Bean Nuclease to create a blunt end. The pCT104 clone (encoding C-terminal MIS sequences) was digested with XbaI, blunted with Mung Bean Nuclease, and subsequently digested with KpnI to release the C-terminal MIS fragment as a KpnI/blunt-end fragment. The C-terminal fragment was ligated to the MEGA promoter:patatin SP to create an in-frame fusion.

After sequence confirmation, the 0.5 kb HindIII/KpnI fragment containing MEGA:patatin SP:C-terminal MIS (FIG. 10) was cloned into the plant transformation vector, pBiB-Kan, which had been digested with HindIII and KpnI. The transgenic plants resulting from transformations using this vector were designated CT116.

Production of C-terminal hMIS in Transgenic Plants

Figure 11:
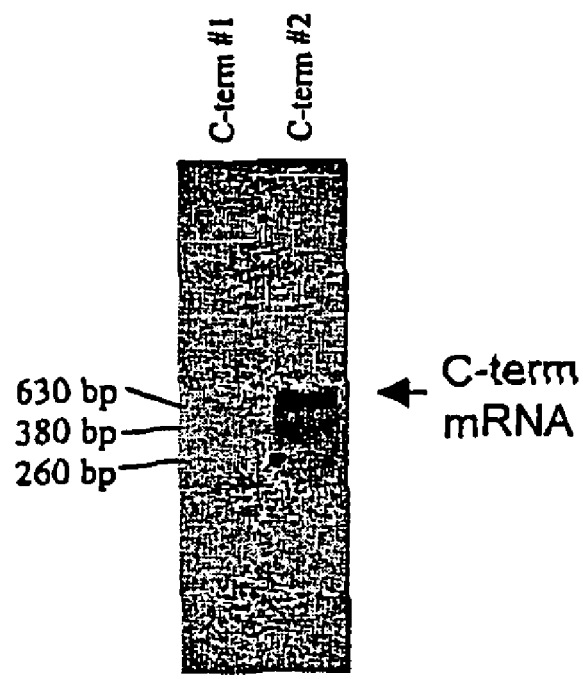

The C-terminal MIS expression construct was introduced into *Agrobacterium tumefaciens* and used to transform tobacco leaf disks by *Agrobacterium*-mediated transformation as described above. Several hundred transgenic plants were isolated and screened for wound-inducible accumulation of the C-terminal MIS transcripts. Northern analysis of total RNA from selected transgenic plants indicated that MIS transcript of the appropriate size (650 bases) was present in these plants (FIG. 11). The C-terminal MIS plants showed a greater level of MIS expression in comparison to the full-length MIS plants. Seeds from the higher expressing C-terminal MIS lines were generated for future use in purification and characterization studies of the protein.

Figure 12:
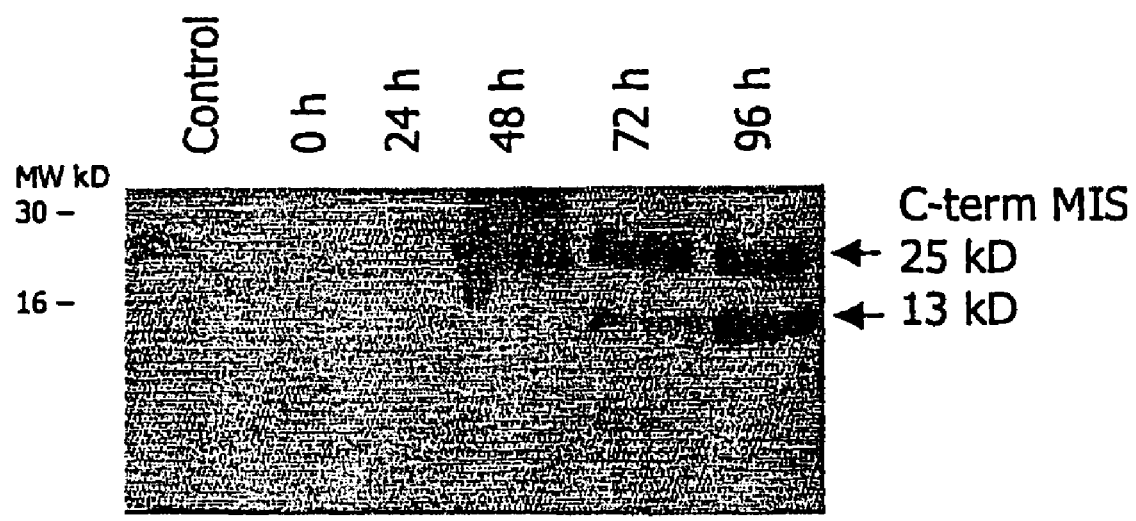

Induction and Characterization of Expression of C-terminal hMIS in Transgenic Plants In order to show that the C-terminal MIS transgenic plants expressed the 12.5 kD protein, tissue from CT116-0036 plants were harvested, wound induced, and incubated at room temperature from 0 to 96 hours. The secreted fraction was collected by rinsing the induced tissue in extract buffer, and proteins from the secreted fraction were analyzed by Western analysis as described above. Samples were analyzed on 15% SDS-PAGE, transferred to membranes and probed with rabbit anti-C terminal MIS antibodies. As shown in FIG. 12, a 25 kD cross-reacting band was present in the 48, 72 and 96 hours samples. A smaller 13 kD protein was present in only the 72 and 96 hr samples. Thus, tobacco produces and secretes the 25 kD dimer as well as the 12.5 kD monomer of C terminal MIS.

Figure 13:
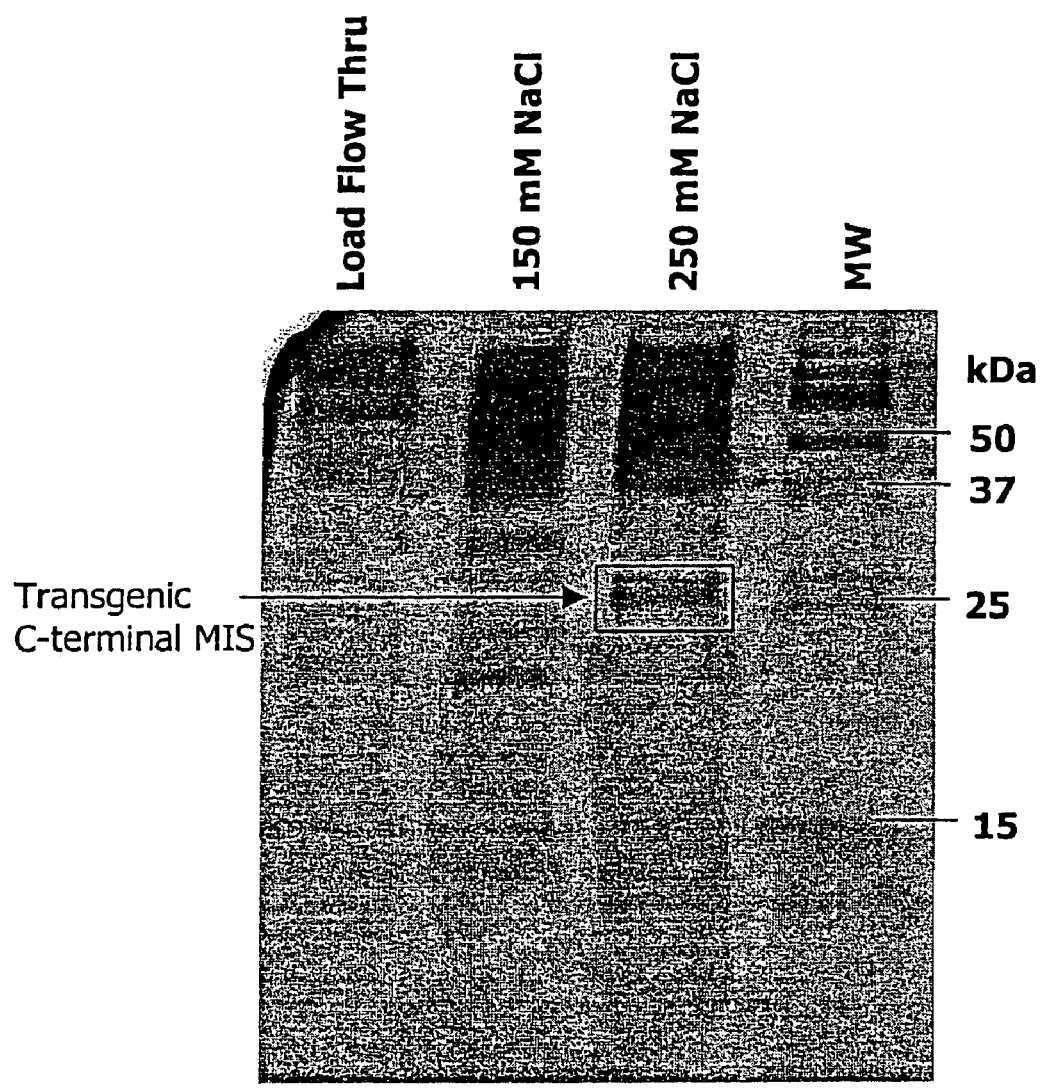

DEAE-cellulose anion exchange chromatography was used as an initial enrichment/purification step (Swann et al., 69 DEV. BIOL. 73-84 (1979)) for plant-derived C-terminal MIS. Secreted fraction from 72 hr wound-induced tissue was concentrated, equilibrated to 20 mM HEPES, pH 8.5, 50 mM NaCl, and loaded onto a DEAE-cellulose column. The C-terminal MIS 25 kD dimer was recovered primarily in the 100 or 250 mM NaCl fraction depending on the column loading and elution conditions based on detection by Western immunoblot analysis. The enrichment of the 25 kD C-terminal protein was visualized using SDS-PAGE gels that were silver-stained to detect total proteins (FIG. 13). Under reducing conditions (sample prepared in presence of dithiothreitol), C-terminal MIS was detected as a 12.5 kD band on SDS-PAGE consistent with reduction of a sulfhydryl bond-linked dimer.

Initial Studies on Biological Activity of Plant-produced C-terminal hMIS

The definitive bioassay for MIS activity involves selective regression of tissues of the fetal rat Müllerian duct. Donahoe et al., 16 BIOL. REPRO. 238-243 (1977); MacLaughlin et al. 198 METH. ENZYMOL. 358-369 (1991). MIS bioactivity of either activated holo-MIS (e.g., enzymatically cleaved with either plasmin or endoproteinase-Lys C) or the dimer C-terminal MIS peptide is measured in a standard fetal rat Müllerian duct regression bioassay that monitors selective regression of the Müllerian duct without affecting the adjacent tissues or the nearby Wolffian duct. Because of the sensitivity of this assay to cytotoxic components, crude proteins preparations (microfiltered and ultrafiltered crude protein concentrates) from various non-transgenic tobacco extracts and secreted fractions were tested for toxicity. All crude tobacco preparations showed some degree of non-specific toxicity on excised embryonic rat urogenital tissues. Thus, partial purification of tobacco-synthesized MIS was required prior to use in the standard fetal rat Müllerian duct regression bioassay.

To test for MIS bioactivity, extracts were prepared from non-transformed control tobacco plants, plants transformed with an "empty" vector, transgenic holo-MIS CT102-0018, and C-terminal MIS CT116-0036 plants and coded such that the bioassay was performed without knowledge of the sample identity. For each sample, 1 kg of biomass was shredded to initiate the wound induction response, incubated for 72 hours, and rinsed with 1 liter of extraction buffer, 20 mM Tris pH 7.4, for 10 min to yield the secreted fractions. These fractions were filtered through miracloth to remove tissue debris, microfiltered, and then collected and concentrated by ultrafiltration as shown in Table 1.

TABLE 1

Microfiltration and Ultrafiltration Steps

| Plant Biomass | MicroFiltration | UltraFiltration |
| --- | --- | --- |
| Non-Transformed | RC100 | RC 5 |
| Vector Alone (Bib-Kan) | RC100 | RC 5 |
| CT102-0018 | BTS 100 | RC 5 |
| CT116-0036 | PES50 | RC 5 |

In order to separate hMIS from tobacco factors toxic to the Müllerian Duct Ridge, the hMIS samples were subjected to purification by lectin chromatography. The holo-MIS will bind and elute from the lectin due to the N-linked glycans. Budzik et al., 21 CELL 909-915 (1980). The C-terminal fragment of MIS does not contain N-linked glycans and therefore has low affinity for the lectin and should be recovered in the flow-through or initial wash fractions. The majority of the toxic compounds were present in the column flow-through. One ml wheat germ lectin columns were prepared. The resin was equilibrated prior to loading the plant extracts by sequential washes of 3 column volumes of the following buffers: loading buffer (20 mM Tris, pH 8.0), wash buffer (20 mM Tris, pH 8.0, 500 mM NaCl), and additional loading buffer. Fifteen milliliters of the ultrafiltered plant extracts were passed through the lectin column and the flow-through fractions were collected. The column was washed with 3 column volumes of loading buffer followed by 3 column volumes of wash buffer. The glycoproteins were eluted with 3 column volumes of elution buffer: 20 mM Tris, pH 8.0, 500 mM N-acetylglucosamine. All samples were analyzed for total protein concentration (Bradford assay) and stored at −80° C. prior to testing for bioactivity.

In order to assess MIS bioactivity, urogenital ridges dissected from 14.5-day-old female fetal rats were incubated with samples comprising 18 μg of total protein from each sample (including ultrafiltered crude extract, column flow-through, Tris column wash, and N-acetylglucosamine elution fraction). After 72 hr, specimens were fixed, embedded in paraffin, sectioned into 8 mm serial sections, and stained. Crude extracts and flow-through fractions from all four plant lines showed non-specific cytotoxicity. Selective Müllerian duct regression was observed only in specimens that had been treated with the Tris wash fractions derived from CT116-0036, the C-terminal MIS plant line. As illustrated in FIG. 14, this treatment caused about an 80% regression of the Müllerian duct with negligible impact on surrounding tissues or the Wolffian duct. The results of this assay demonstrated that plants were capable of producing a C-terminal MIS dimer that shows definitive MIS bioactivity. In contrast, none of the control tobacco fractions or the CT102-0018 holo-MIS samples exhibited bioactivity. The negative result with CT102-0018 samples was expected because the holo-MIS had not been "activated" by enzymatic cleavage to release the active C-terminal fragment prior to performing the assay. Further purification of plant-derived holo-MIS from CT102-0018 is required in order to subject the holo-MIS to plasmin-mediated cleavage for release of the active C-terminal MIS fragment and bioactivity assessment.

All references, patents, or applications cited herein are incorporated herein by reference in their entirety, as if written herein.

We claim:

1. A method for producing a bioactive recombinant Transforming Growth Factor-β (TGF-β) protein in vivo in a plant host system, comprising transforming said plant host system with a chimeric nucleic acid sequence that encodes a TGF-β protein wherein said chimeric nucleic acid sequence comprises a first nucleic acid sequence that regulates transcription in said plant host system, a second nucleic acid sequence encoding a signal sequence and a third nucleic acid sequence encoding a full length bioactive TGF-β protein or a bioactive TGF-β protein C-terminal fragment; cultivating the transformed plant host system under conditions to express said bioactive TGF-β protein in vivo; and recovering said in vivo expressed bioactive TGF-β protein from said transformed plant host system.

2. The method of claim 1. wherein said bioactive TGF-β protein is selected from a group consisting of TGF-β, TGF-$\beta_2$, TGF-$\beta_3$, TGF-$\beta_4$, TGF-$\beta_5$, Growth/Differentiation Factor (GDF) isoforms, Vg-1, Inhibins, Activins, Müllerian Inhibiting Substance (MIS), decapentaplegic protein (dpp), and Bone Morphogenetic proteins (BMP).

3. The method of claim 1, wherein said bioactive TGF-β protein is a human MIS protein.

4. The method of claim 1, wherein said first nucleic acid is a plant-active promoter.

5. The method of claim 4, wherein said plant-active promoter is a constitutive promoter, a developmentally regulated promoter, a tissues-specific promoter, or an inducible promoter.

6. The method of claim 1, wherein said chimeric nucleic acid sequence comprises an expression cassette capable of expressing said bioactive TGF-β protein in plant cells.

7. The method of claim 1, wherein said bioactive TGF-β protein exhibits biological activity in a definitive cell-based or tissue-based test system.

8. The method of claim 7, wherein said bioactive TGF-β protein is a MIS protein.

9. The method of claim 8, wherein said definitive biological activity test system comprises the Mullerian Duct Regression Assay.

10. The method of claim 1, wherein said plant host system comprises a monocotyledonous plant or plant cell.

11. The method of claim 1, wherein said plant host system comprises a dicotyledonous plant or plant cell.

12. The method of claim 10, wherein said monocotyledonous plant or plant cell is a lily, a grass, corn, rice, oat, wheat, barley, orchid, iris, onion, or palm.

13. The method according to claim 11, wherein said dicotyledonous plant or plant cell is tobacco, tomato, potato, alfalfa, soybean, oak, maple, rose, mint, squash, daisy, walnut, cactus, violet, or buttercup.

* * * * *

UNITED STATES PATENT AND TRADEMARK OFFICE
CERTIFICATE OF CORRECTION

PATENT NO. : 8,058,512 B2
APPLICATION NO. : 11/268741
DATED : November 15, 2011
INVENTOR(S) : Karen Oishi and Leonard M. Comaratta It is certified that error appears in the above-identified patent and that said Letters Patent is hereby corrected as shown below:

Column 7,
Line 28, "McGA™" should read -- MeGA™--.
Line 31, "McGA™" should read -- MeGA™--.
Line 46, "McGA™" should read -- MeGA™--.
Line 49, "McGA™" should read -- MeGA™--.

Column 8,
Line 17, "L1 et al.," should read --Li et al.,--.
Lines 22-23, "During et al.," should read --Düring et al.,--.

Column 25,
Line 10, "Vol. 11984," should read --Vol. I 1984,--.

Column 26,
Line 52, "pRiB-Kan" should read --pBiB-Kan--.

Signed and Sealed this
Seventeenth Day of April, 2012

David J. Kappos
*Director of the United States Patent and Trademark Office*

SEQUENCE LISTING

<160> NUMBER OF SEQ ID NOS: 12

<210> SEQ ID NO 1
<211> LENGTH: 1683
<212> TYPE: DNA
<213> ORGANISM: Homo sapiens

<400> SEQUENCE: 1

```
atgcgggacc tgcctctcac cagcctggcc ctagtgctgt ctgccctggg ggctctgctg      60
gggactgagg ccctcagagc agaggagcca gctgtgggca ccagtggcct catcttccga     120
gaagacttgg actggcctcc aggcatccca caagagcctc tgtgcctggt ggcactgggc     180
ggggacagca atggcagcag ctcccccctg cgggtggtgg gggctctaag cgcctatgag     240
caggccttcc tgggggccgt gcagagggcc cgctgggcc cccgagacct ggccaccttc     300
ggggtctgca acaccggtga caggcaggct gccttgccct ctctacggcg gctggggcc     360
tggctgcggg accctggggg gcagcgcctg gtggtcctac acctggagga agtgacctgg     420
gagccaacac cctcgctgag gttccaggag ccccgcctg gaggagctgg ccccccagag     480
ctggcgctgc tggtgctgta ccctgggcct ggccctgagg tcactgtgac gagggctggg     540
ctgccgggtg cccagagcct ctgcccctcc cgagacaccc gctacctggt gttagcggtg     600
gaccgccctg cggggccctg gcgcggctcc gggctggcct tgaccctgca gccccgcgga     660
gaggactccc ggctgagtac cgcccggctg caggcactgc tgttcggcga cgaccaccgc     720
tgcttcacac ggatgacccc ggccctgctc ctgctgccgc ggtccgagcc cgcgccgctg     780
cctgcgcacg gccagctgga caccgtgccc ttcccgccgc ccaggccatc cgcggaactc     840
gaggagtcgc cacccagcgc agaccccttc ctggagacgc tcacgcgcct ggtgcgggcg     900
ctgcgggtcc ccccggcccg ggcctccgcg ccgcgcctgg ccctggatcc ggacgcgctg     960
gccggcttcc cgcagggcct agtcaacctg tcggaccccg cggcgctgga gcgcctactc    1020
gacggcgagg agccgctgct gctgctgctg aggcccactg cggccaccac cggggatcct    1080
gcgcccctgc acgaccccac gtcggcgccg tgggccacgg ccctggcgcg ccgcgtggct    1140
gctgaactgc aagcggcggc tgccgagctg cgaagcctcc cgggtctgcc tccggccaca    1200
gccccgctgc tggcgcgcct gctcgcgctc tgcccaggag gccccggcgg cctcggcgat    1260
ccctgcgag cgctgctgct cctgaaggcg ctgcagggcc tgcgcgtgga gtggcgcggg    1320
cgggatccgc gcgggccggg tcgggcacag cgcagcgcgg gggccaccgc cgccgacggg    1380
ccgtgcgcgc tgcgcgagct cagcgtagac ctccgcgccg agcgctccgt actcatcccc    1440
gagacctacc aggccaacaa ttgccagggc gtgtgcggct ggcctcagtc cgaccgcaac    1500
ccgcgctacg gcaaccacgt ggtgctgctg ctgaagatgc aggcccgtgg ggccgccctg    1560
gcgcgcccac cctgctgcgt gcccaccgcc tacgcgggca agctgctcat cagcctgtcg    1620
gaggaacgca tcagcgcgca ccacgtgccc aacatggtgg ccaccgagtg tggctgccgg    1680
tga                                                                  1683
```

<210> SEQ ID NO 2

-continued

<211> LENGTH: 480
<212> TYPE: DNA
<213> ORGANISM: Homo sapiens

<400> SEQUENCE: 2

```
caatacgata ttaccgaata ttatactaaa tcaaaattta atttatcata tcgaattatt    60
aaactgatat ttcaaatttt aatatttaat atctactttc aactattatt acctaattat   120
caaatgcaaa atgtatgagt tatttcataa tagcccgagt tcgtatccaa atattttaca   180
cttgaccagt caacttgact atataaaact ttacttcaaa aaattaaaaa aaaaagaaag   240
tatattattg taaagataa tactccattc aaaatataaa atgaaaaaag tccagcgcgg    300
caaccgggtt cctctataaa tacatttcct acatcttctc ttctcctcac atcccatcac   360
tcttctttta acaattatac ttgtcaatca tcaatcccac aaacaacact ttttctctcc   420
tcttttttcct caccggcggc agacttaccg gtgaaatcta gagtaagcat catgaattcc  480
```

<210> SEQ ID NO 3
<211> LENGTH: 480
<212> TYPE: DNA
<213> ORGANISM: Homo sapiens

<400> SEQUENCE: 3

```
gttatgctat aatggcttat aatatgattt agttttaaat taaatagtat agcttaataa    60
tttgactata aagtttaaaa ttataaatta tagatgaaag ttgataataa tggattaata   120
gtttacgttt tacatactca ataaagtatt atcgggctca agcataggtt tataaaatgt   180
gaactggtca gttgaactga tatattttga aatgaagttt tttaattttt tttttcttc   240
atataataac attttctatt atgaggtaag tttatatttt tacttttttc aggtcgcgcc   300
gttggcccaa ggagatattt atgtaaagga tgtagaagag aagaggagtg tagggtagtg  360
agaagaaaat tgttaatatg aacagttagt agttagggtg tttgttgtga aaaagagagg  420
agaaaaagga gtggccgccg tctgaatggc cactttagat ctcattcgta gtacttaagg  480
```

<210> SEQ ID NO 4
<211> LENGTH: 28
<212> TYPE: DNA
<213> ORGANISM: Artificial Sequence
<220> FEATURE:
<223> OTHER INFORMATION: MS3 5' Primer

<400> SEQUENCE: 4

```
ggtctagaag cgcggggggcc accgccgc                                      28
```

<210> SEQ ID NO 5
<211> LENGTH: 28
<212> TYPE: DNA
<213> ORGANISM: Artificial Sequence
<220> FEATURE:
<223> OTHER INFORMATION: MS4 3' Primer

<400> SEQUENCE: 5

```
ggggtacctc accggcagcc acactcgg                                       28
```

<210> SEQ ID NO 6
<211> LENGTH: 560
<212> TYPE: PRT
<213> ORGANISM: Homo sapiens

<400> SEQUENCE: 6

```
Met Arg Asp Leu Pro Leu Thr Ser Leu Ala Leu Val Leu Ser Ala Leu
1               5                   10                  15
```

```
Gly Ala Leu Leu Gly Thr Glu Ala Leu Arg Ala Glu Pro Ala Val
             20                  25                  30
Gly Thr Ser Gly Leu Ile Phe Arg Glu Asp Leu Asp Trp Pro Gly
         35                  40                  45
Ile Pro Gln Glu Pro Leu Cys Leu Val Ala Leu Gly Gly Asp Ser Asn
     50                  55                  60
Gly Ser Ser Ser Pro Leu Arg Val Val Gly Ala Leu Ser Ala Tyr Glu
 65                  70                  75                  80
Gln Ala Phe Leu Gly Ala Val Gln Arg Ala Arg Trp Gly Pro Arg Asp
                 85                  90                  95
Leu Ala Thr Phe Gly Val Cys Asn Thr Gly Asp Arg Gln Ala Ala Leu
            100                 105                 110
Pro Ser Leu Arg Arg Leu Gly Ala Trp Leu Arg Asp Pro Gly Gly Gln
            115                 120                 125
Arg Leu Val Val Leu His Leu Glu Glu Val Thr Trp Glu Pro Thr Pro
130                 135                 140
Ser Leu Arg Phe Gln Glu Pro Pro Gly Gly Ala Gly Pro Pro Glu
145                 150                 155                 160
Leu Ala Leu Leu Val Leu Tyr Pro Gly Pro Gly Glu Val Thr Val
                165                 170                 175
Thr Arg Ala Gly Leu Pro Gly Ala Gln Ser Leu Cys Pro Ser Arg Asp
            180                 185                 190
Thr Arg Tyr Leu Val Leu Ala Val Asp Arg Pro Ala Gly Ala Trp Arg
        195                 200                 205
Gly Ser Gly Leu Ala Leu Thr Leu Gln Pro Arg Gly Glu Asp Ser Arg
    210                 215                 220
Leu Ser Thr Ala Arg Leu Gln Ala Leu Leu Phe Gly Asp Asp His Arg
225                 230                 235                 240
Cys Phe Thr Arg Met Thr Pro Ala Leu Leu Leu Pro Arg Ser Glu
                245                 250                 255
Pro Ala Pro Leu Pro Ala His Gly Gln Leu Asp Thr Val Pro Phe Pro
            260                 265                 270
Pro Pro Arg Pro Ser Ala Glu Leu Glu Glu Ser Pro Pro Ser Ala Asp
        275                 280                 285
Pro Phe Leu Glu Thr Leu Thr Arg Leu Val Arg Ala Leu Arg Val Pro
    290                 295                 300
Pro Ala Arg Ala Ser Ala Pro Arg Leu Ala Leu Asp Pro Asp Ala Leu
305                 310                 315                 320
Ala Gly Phe Pro Gln Gly Leu Val Asn Leu Ser Asp Pro Ala Ala Leu
                325                 330                 335
Glu Arg Leu Leu Asp Gly Glu Glu Pro Leu Leu Leu Leu Arg Pro
            340                 345                 350
Thr Ala Ala Thr Thr Gly Asp Pro Ala Pro Leu His Asp Pro Thr Ser
        355                 360                 365
Ala Pro Trp Ala Thr Ala Leu Ala Arg Arg Val Ala Ala Glu Leu Gln
    370                 375                 380
Ala Ala Ala Ala Glu Leu Arg Ser Leu Pro Gly Leu Pro Ala Thr
385                 390                 395                 400
Ala Pro Leu Leu Ala Arg Leu Leu Ala Leu Cys Pro Gly Gly Pro Gly
                405                 410                 415
Gly Leu Gly Asp Pro Leu Arg Ala Leu Leu Leu Lys Ala Leu Gln
            420                 425                 430
Gly Leu Arg Val Glu Trp Arg Gly Arg Asp Pro Arg Gly Pro Gly Arg
```

Ala Gln Arg Ser Ala Gly Ala Thr Ala Ala Asp Gly Pro Cys Ala Leu
    450                 455                 460

Arg Glu Leu Ser Val Asp Leu Arg Ala Glu Arg Ser Val Leu Ile Pro
465                 470                 475                 480

Glu Thr Tyr Gln Ala Asn Asn Cys Gln Gly Val Cys Gly Trp Pro Gln
                485                 490                 495

Ser Asp Arg Asn Pro Arg Tyr Gly Asn His Val Val Leu Leu Leu Lys
            500                 505                 510

Met Gln Ala Arg Gly Ala Ala Leu Ala Arg Pro Pro Cys Cys Val Pro
        515                 520                 525

Thr Ala Tyr Ala Gly Lys Leu Leu Ile Ser Leu Ser Glu Glu Arg Ile
    530                 535                 540

Ser Ala His His Val Pro Asn Met Val Ala Thr Glu Cys Gly Cys Arg
545                 550                 555                 560

<210> SEQ ID NO 7
<211> LENGTH: 330
<212> TYPE: DNA
<213> ORGANISM: Homo sapiens

<400> SEQUENCE: 7
agcgcggggg ccaccgccgc cgacgggccg tgcgcgctgc gcgagctcag cgtagacctc      60
cgcgccgagc gctccgtact catccccgag acctaccagg ccaacaattg ccagggcgtg     120
tgcggctggc ctcagtccga ccgcaacccg cgctacggca accacgtggt gctgctgctg     180
aagatgcagg cccgtggggc cgccctggcg cgcccaccct gctgcgtgcc caccgcctac     240
gcgggcaagc tgctcatcag cctgtcggag aacgcatca gcgcgcacca cgtgcccaac     300
atggtggcca ccgagtgtgg ctgccggtga                                       330

<210> SEQ ID NO 8
<211> LENGTH: 109
<212> TYPE: PRT
<213> ORGANISM: Homo sapiens

<400> SEQUENCE: 8

Ser Ala Gly Ala Thr Ala Ala Asp Gly Pro Cys Ala Leu Arg Glu Leu
1               5                   10                  15

Ser Val Asp Leu Arg Ala Glu Arg Ser Val Leu Ile Pro Glu Thr Tyr
            20                  25                  30

Gln Ala Asn Asn Cys Gln Gly Val Cys Gly Trp Pro Gln Ser Asp Arg
        35                  40                  45

Asn Pro Arg Tyr Gly Asn His Val Val Leu Leu Leu Lys Met Gln Ala
    50                  55                  60

Arg Gly Ala Ala Leu Ala Arg Pro Pro Cys Cys Val Pro Thr Ala Tyr
65                  70                  75                  80

Ala Gly Lys Leu Leu Ile Ser Leu Ser Glu Glu Arg Ile Ser Ala His
                85                  90                  95

His Val Pro Asn Met Val Ala Thr Glu Cys Gly Cys Arg
            100                 105

<210> SEQ ID NO 9
<211> LENGTH: 69
<212> TYPE: DNA
<213> ORGANISM: Homo sapiens

<400> SEQUENCE: 9

```
atggcaacta ctaaatcttt tttaatttta ttttttatga tattagcaac tactagttca    60
acatgtgcg                                                             69

<210> SEQ ID NO 10
<211> LENGTH: 23
<212> TYPE: PRT
<213> ORGANISM: Homo sapiens

<400> SEQUENCE: 10

Met Ala Thr Thr Lys Ser Phe Leu Ile Leu Phe Phe Met Ile Leu Ala
1               5                   10                  15

Thr Thr Ser Ser Thr Cys Ala
            20

<210> SEQ ID NO 11
<211> LENGTH: 545
<212> TYPE: DNA
<213> ORGANISM: Homo sapiens

<400> SEQUENCE: 11
caatacgata ttaccgaata ttatactaaa tcaaaattta atttatcata tcgaattatt    60
aaactgatat ttcaaatttt aatatttaat atctactttc aactattatt acctaattat   120
caaatgcaaa atgtatgagt tatttcataa tagcccgagt tcgtatccaa atattttaca   180
cttgaccagt caacttgact atataaaact ttacttcaaa aaattaaaaa aaaaagaaag   240
tatattattg taaaagataa tactccattc aaaatataaa atgaaaaaag tccagcgcgg   300
caaccgggtt cctctataaa tacatttcct acatcttctc ttctcctcac atcccatcac   360
tcttctttta acaattatac ttgtcaatca tcaatcccac aaacaacact ttttctctcc   420 tcttttcct caccggcggc agacttaccg gtgaaatcta gagtaagcat catggcaact   480
actaaatctt ttttaatttt atttttatg atattagcaa ctactagttc aacatgtgcg   540
gtacc                                                               545

<210> SEQ ID NO 12
<211> LENGTH: 545
<212> TYPE: DNA
<213> ORGANISM: Homo sapiens

<400> SEQUENCE: 12
gttatgctat aatggcttat aatatgattt agttttaaat taaatagtat agcttaataa    60
tttgactata aagtttaaaa ttataaatta tagatgaaag ttgataataa tggattaata   120
gtttacgttt tacatactca ataaagtatt atcgggctca agcataggtt tataaaatgt   180
gaactggtca gttgaactga tatatttga aatgaagttt tttaattttt tttttctttc   240
atataataac attttctatt atgaggtaag tttatattt tacttttttc aggtcgcgcc   300
gttggcccaa ggagatattt atgtaaagga tgtagaagag aagaggagtg tagggtagtg   360
agaagaaaat tgttaatatg aacagttagt agttagggtg tttgttgtga aaagagagg   420 agaaaaagga gtggccgccg tctgaatggc cactttagat ctcattcgta gtaccgttga   480
tgatttagaa aaaattaaaa taaaaatac tataatcgtt gatgatcaag ttgtacacgc   540
catgg                                                               545
```